(12) United States Patent
Chung et al.

(10) Patent No.: US 10,464,307 B2
(45) Date of Patent: Nov. 5, 2019

(54) LAYERLESS BIOPRINTING VIA DYNAMIC OPTICAL PROJECTION AND USES THEREOF

(71) Applicant: THE REGENTS OF THE UNIVERSITY OF CALIFORNIA, Oakland, CA (US)

(72) Inventors: Peter Chung, San Diego, CA (US); Xin Qu, Houston, TX (US); Aping Zhang, Hangzhou (CN); Shaochen Chen, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 297 days.

(21) Appl. No.: 15/311,135

(22) PCT Filed: May 20, 2015

(86) PCT No.: PCT/US2015/031848
§ 371 (c)(1),
(2) Date: Nov. 14, 2016

(87) PCT Pub. No.: WO2015/179572
PCT Pub. Date: Nov. 26, 2015

(65) Prior Publication Data
US 2017/0087766 A1 Mar. 30, 2017

Related U.S. Application Data

(60) Provisional application No. 62/001,025, filed on May 20, 2014.

(51) Int. Cl.
*B29C 35/08* (2006.01)
*B33Y 30/00* (2015.01)
(Continued)

(52) U.S. Cl.
CPC .......... *B33Y 80/00* (2014.12); *B29C 35/0805* (2013.01); *B29C 35/0894* (2013.01);
(Continued)

(58) Field of Classification Search
CPC ........ B29C 2035/0838; B29C 2035/08; B29C 2035/0827; B29C 64/277; B29C 64/386;
(Continued)

(56) References Cited

U.S. PATENT DOCUMENTS 4,961,154 A 10/1990 Pomerantz et al.
5,484,314 A * 1/1996 Farnworth .............. H01J 9/242
445/24
(Continued)

FOREIGN PATENT DOCUMENTS

WO 2014074954 A2 5/2014

OTHER PUBLICATIONS

Suri, S., Han, L., Zhang, W., Singh, A., Chen, S., & Schmidt, C. E. (2011). Solid freeform fabrication of designer scaffolds of hyaluronic acid for nerve tissue engineering. Biomedical Microdevices, 13(6), 983-993. doi:10.1007/s10544-011-9568-9 (Year: 2011).*
(Continued)

*Primary Examiner* — Anthony Calandra
*Assistant Examiner* — Caroline Montiel
(74) *Attorney, Agent, or Firm* — Eleanor Musick; Musick Davison LLP

(57) ABSTRACT

A system and method for 3D microfabrication projects light capable of initiating photopolymerization toward a spatial light modulator that modulates light responsive to digital masks corresponding to layers of the structure. Projection optics focus the modulated light onto an optical plane within a photopolymerizable material supported on a stage. A computer controller causes the spatial light modulator to project a sequence of images corresponding to the digital
(Continued)

masks while coordinating movement of the stage to move a position of the optical plane within the photopolymerizable material to sequentially project each image of the sequence to generate the structure by progressively photopolymerizing the photopolymerizable material.

29 Claims, 24 Drawing Sheets

(51) Int. Cl.
| | | |
|---|---|---|
| B33Y 50/02 | (2015.01) | |
| B29C 64/129 | (2017.01) | |
| B33Y 80/00 | (2015.01) | |
| B33Y 10/00 | (2015.01) | |
| B33Y 70/00 | (2015.01) | |
| G01N 33/50 | (2006.01) | |
| B29C 64/386 | (2017.01) | |
| B29C 64/40 | (2017.01) | |
| B29C 64/277 | (2017.01) | |
| B29L 31/00 | (2006.01) | |

(52) U.S. Cl.
CPC .......... *B29C 64/129* (2017.08); *B29C 64/277* (2017.08); *B29C 64/386* (2017.08); *B29C 64/40* (2017.08); *B33Y 10/00* (2014.12); *B33Y 30/00* (2014.12); *B33Y 50/02* (2014.12); *B33Y 70/00* (2014.12); *G01N 33/502* (2013.01); *G01N 33/5058* (2013.01); *B29C 2035/0827* (2013.01); *B29C 2035/0838* (2013.01); *B29K 2995/0005* (2013.01); *B29K 2995/0056* (2013.01); *B29L 2031/752* (2013.01); *B29L 2031/7532* (2013.01)

(58) Field of Classification Search
CPC .............. B29C 64/129; B29C 35/0894; B29C 35/0805; B33Y 10/00; B33Y 30/00; G01N 33/502; G01N 33/5058; B29K 2995/0056; B29L 2031/752
See application file for complete search history.

(56) References Cited

U.S. PATENT DOCUMENTS

| | | | |
|---|---|---|---|
| 5,545,367 A * | 8/1996 | Bae | ........................ B33Y 50/02 264/401 |
| 5,938,954 A * | 8/1999 | Onuma | .............. B23K 26/1224 219/121.6 |
| 8,444,899 B2 | 5/2013 | DeSimone et al. | |
| 9,631,171 B2 | 4/2017 | Soman et al. | |
| 2004/0023434 A1 | 2/2004 | Venkatesan et al. | |
| 2005/0234513 A1 | 10/2005 | Alexander et al. | |
| 2005/0259785 A1 | 11/2005 | Zhang | |
| 2006/0069230 A1 | 3/2006 | Papisov | |
| 2006/0100734 A1 * | 5/2006 | Huang | ................... B33Y 10/00 700/119 |
| 2006/0267997 A1 | 11/2006 | Walls et al. | |
| 2006/0267998 A1 | 11/2006 | Walls et al. | |
| 2007/0259156 A1 * | 11/2007 | Kempers | ............. B81C 1/00206 428/188 |
| 2007/0292837 A1 | 12/2007 | Deutsch et al. | |
| 2009/0233359 A1 | 9/2009 | Kwon | |
| 2011/0033887 A1 * | 2/2011 | Fang | ................. B01L 3/502707 435/41 |
| 2012/0241740 A1 * | 9/2012 | Park | .................... H01L 27/1288 257/49 |
| 2013/0044300 A1 | 2/2013 | Mei et al. | |
| 2013/0123988 A1 | 5/2013 | Jariwala et al. | |
| 2013/0295212 A1 * | 11/2013 | Chen | ..................... B29C 64/129 425/150 |
| 2013/0344601 A1 | 12/2013 | Soman et al. | |
| 2016/0046072 A1 | 2/2016 | Rolland et al. | |
| 2016/0298087 A1 | 10/2016 | Qu et al. | |
| 2017/0283766 A1 | 10/2017 | Hribar et al. | |

OTHER PUBLICATIONS

Feng, X, et al. Visualization of Dynamic Trafficking of a Protein Kinase C ßII/Green Fluorescent Protein Conjugate Reveals Differences in G Protein-coupled Receptor Activation and Desensitization, Journal of Biological Chemistry, vol. 273, No. 17, Apr. 24, 1998, 10755-10762.

Grogan, S.P. et al., Digital micromirror device projection printing system for meniscus tissue engineering, Acta Biomaterialia 9 (2013) 7218-7226.

Han, L-H, et al., Fabrication of three-dimensional scaffolds for heterogeneous tissue engineering, Biomed Microdevices, Springer Science+Business Media LLC 2010, DOI 10.1007/s10544-010-9425-2, 4 pgs.

Han, L-H, et al., Projection Microfabrication of Three-Dimensional Scaffolds for Tissue Engineering, Journal of Manufacturing Science and Engineering, Apr. 2008, vol. 130 / 021005-1, 5 pgs.

Hiribar, K.C. et al., Light-assisted direct-write of 3D functional biomaterials; Lab Chip, 2014, 14, 268-275.

PCT/US2015/031848, International Search Report and Written Opinion, dated Aug. 5, 2015, 12 pages.

Soman et al., Digital microfabrication of user-defined 3D microstructures in cell-laden hydrogels, Jun. 3, 2013, Biotechnol Bioeng, 110(11): 3038-3047.

Zhang, A.P. et al., Rapid Fabrication of Complex 3D Extracellular Microenvironments by Dynamic Optical Projection Stereolithography, Adv. Mater. 2012, 24 4266-4270.

EP15795499.1 Extended European Search Report dated Dec. 22, 2017, 7 pgs.

* cited by examiner

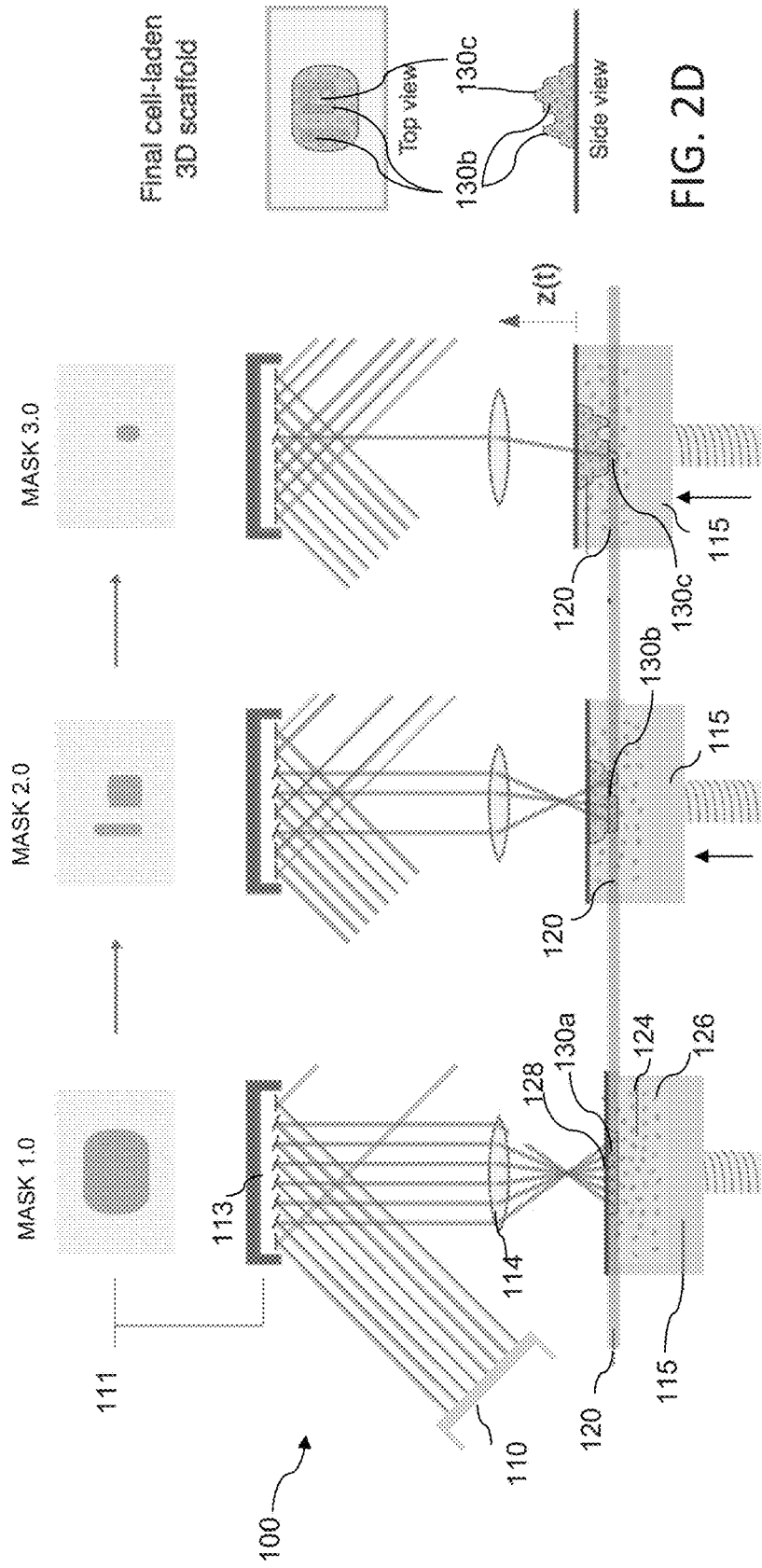

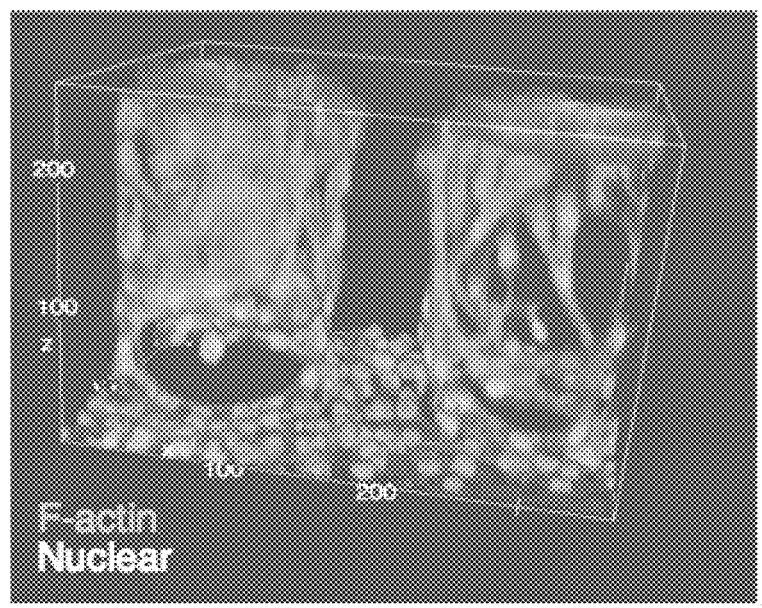
FIG. 4A
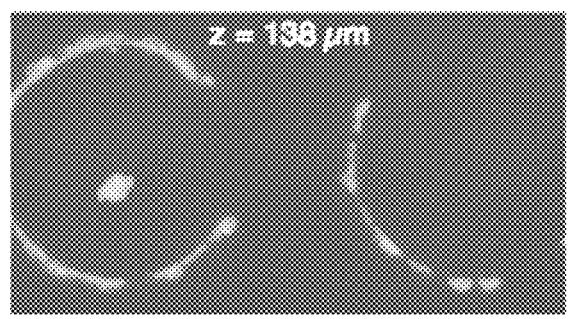
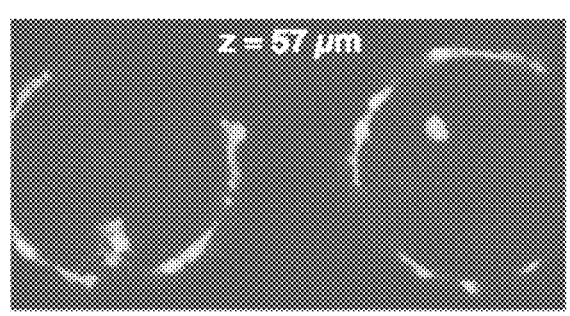
FIG. 4B
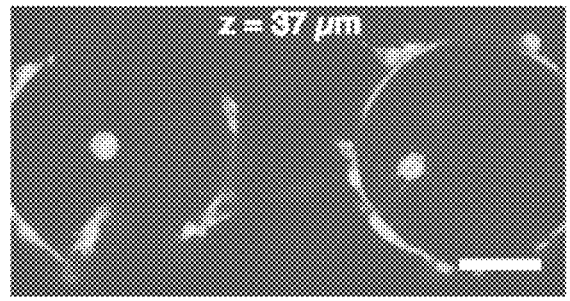

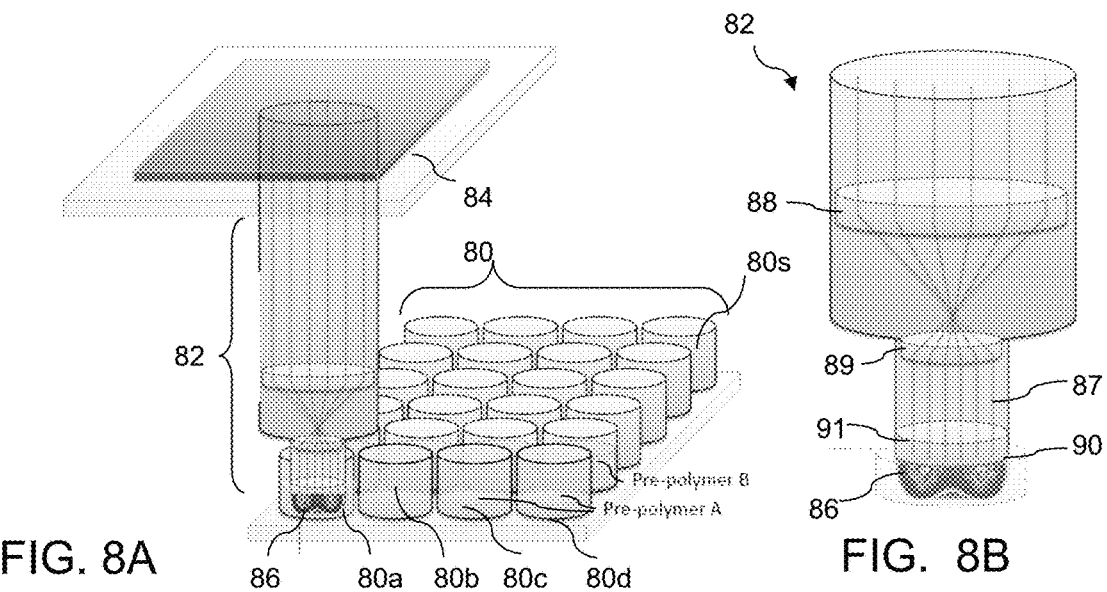
FIG. 8A
FIG. 8B
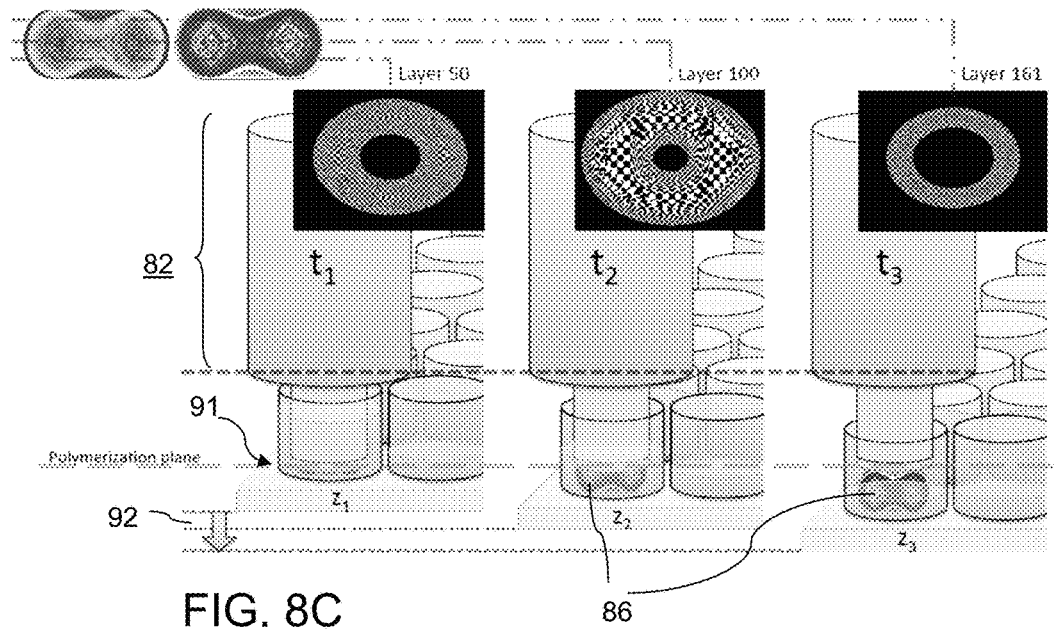
FIG. 8C

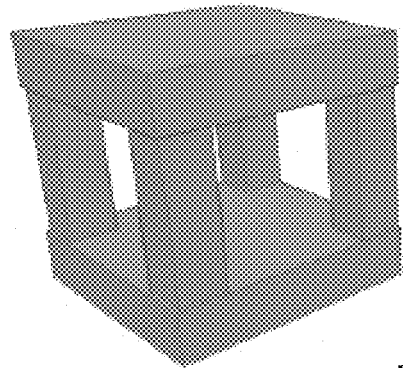
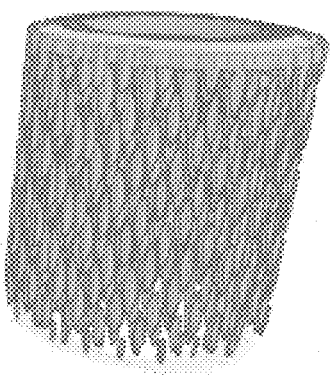
FIG. 9A
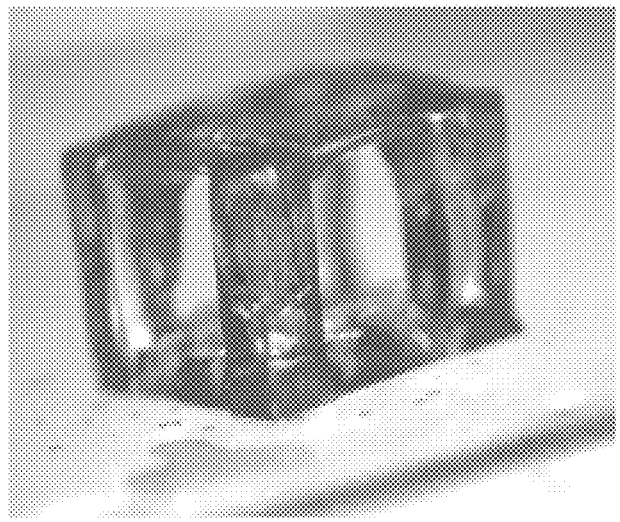
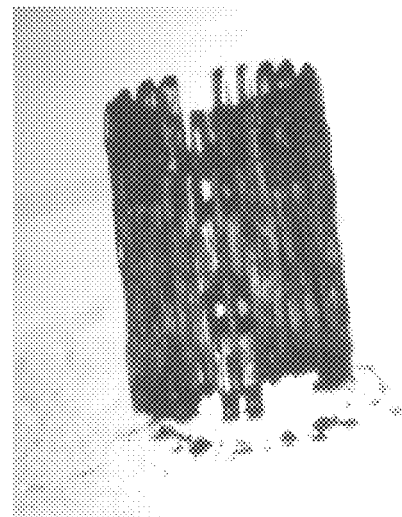
FIG. 9B

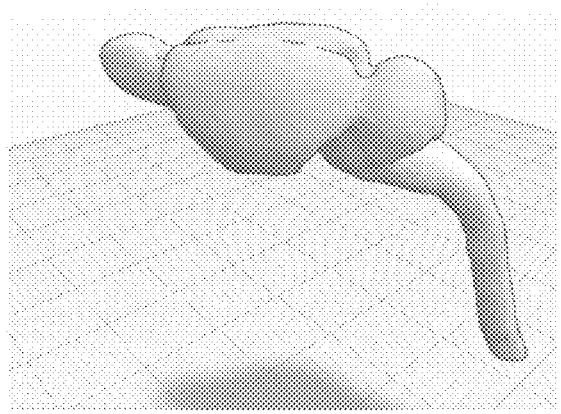
FIG. 13A
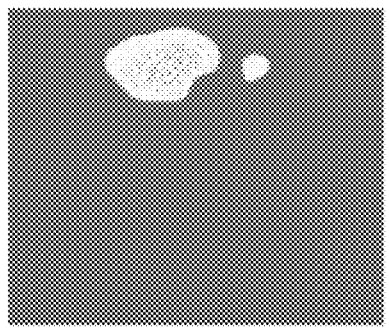 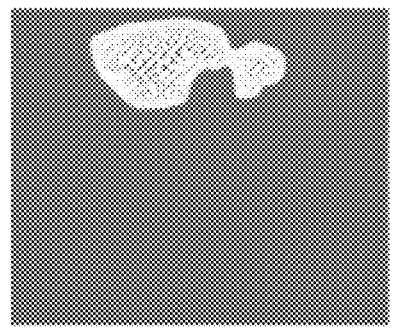
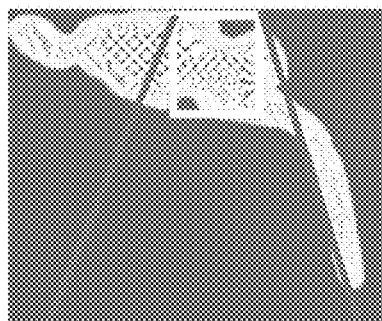 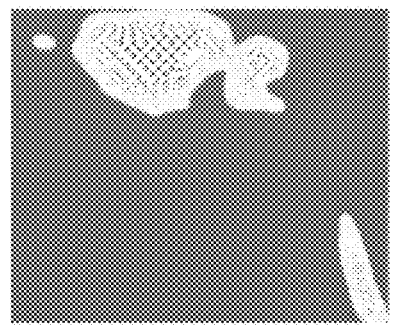
FIG. 13B
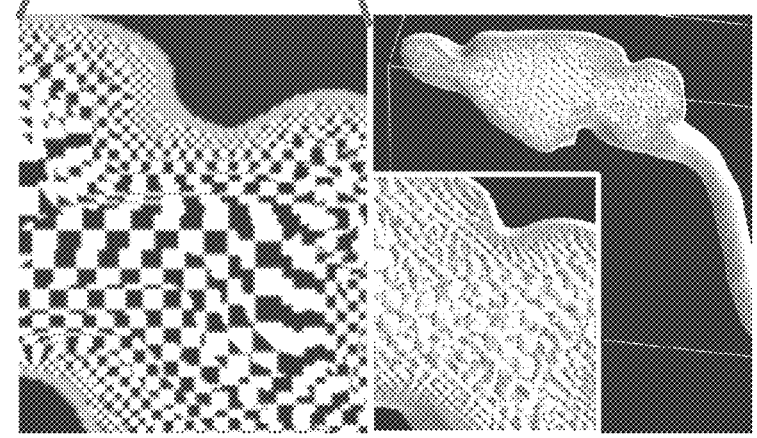
FIG. 13C

LAYERLESS BIOPRINTING VIA DYNAMIC OPTICAL PROJECTION AND USES THEREOF

RELATED APPLICATIONS

The present application is a 371 national stage filing of International Application No. PCT/US2015/031848, filed May 20, 2015, which claims the benefit of the priority of U.S. Provisional Application No. 62/001,025, filed May 20, 2014, each of which is incorporated herein by reference in its entirety.

GOVERNMENT RIGHTS

This invention was made with government support under Grant No. EB012597 awarded by the National Institutes of Health. The government has certain rights in the invention.

FIELD OF THE INVENTION

The present invention relates to a method for microfabrication of three-dimensional structures in photopolymers and fabricating biological scaffolds with smooth (layerless) contours.

BACKGROUND OF THE INVENTION

Traditional cell culture is usually carried out in a Petri dish, and most commonly used cell biological techniques rely on the use of cultured cells on 2D platforms. As is known, the mechanical properties of cell substrates affect cell differentiation, growth and motility. Thus, the mechanical properties of a material are important to consider when designing a cell scaffold. To mimic an actual cell environment, it is imperative to create 3D functional tissue models using 3D biomanufacturing methods rather than 2D patterning ones. In addition, the manufacturing process and/or materials must be cell-friendly. Current fabrication systems for biological scaffolds utilize approaches such as bio-inkjet printing and raster laser projection, which are limited in scalability and speed, and cannot create complex structures and scalable tissue construct. Cast molding approaches can achieve basic geometries but cannot reproduce complex 3D geometries with intricate biomimetic features and aspect ratios. Laser micro-stereolithography (laser-μSL) techniques have grown to be popular for their abilities to create 3D scaffolds [Mapili et al., 2005; Gansel et al., 2009]. However, scaffold fabrication using laser-μSL is usually slow due to point-by-point laser scanning Many existing layer-by-layer stereolithographic methods do not feature a dynamically changing mask and simultaneous stage movement and therefore cause undesired layer artifacts that may alter cellular responses and not reflect the true native physiology.

One approach that has been commercialized by Carbon3D, Inc. (Redwood City, Calif.) for immersion printing of polymer nanostructures involves projecting an image through the transparent floor of a liquid resin reservoir while gradually lifting an immersed substrate away from the floor as the resin is cured on the bottom of the substrate. The oxygen permeable transparent floor of the bath allows for a "dead zone" of dissolved oxygen to inhibit polymerization at the floor of the bath. The techniques used in the Carbon3D system are described in numerous U.S. patents, issued and pending, to Joseph M. DeSimone, et al., including U.S. Pat. No. 8,263,129, which is incorporated herein by reference. The reservoir and substrate of the Carbon3D system remain stationary, with only the immersed substrate moving within the z-axis to lift the printed object away from the floor as printing advances, which limits the varieties of shapes that can be created. Further, the technology's reliance on immersion limits the types and combinations of materials that may be used.

Conventional stereolithographic approaches are not well suited for high-throughput fabrication of complex cell-supportive 3D microstructures, particularly within substrates such as multi-well plates that are commonly used in the life sciences. These shortcomings severely limit widespread adoption of 3D printed cell culture methods since researchers often rely on products configured to interface with commonly used lab instruments integral to established experimental workflows. Multi-well cell culture plates (in addition to microscope slides, Petri dishes, cell culture flasks, etc.) often serve as the de facto standard upon which specialized culture environments are designed. Many 3D hydrogel cell culture platforms feature biocompatible and/or biologically-derived materials that have been polymerized or otherwise manufactured, albeit typically as unpatterned bulk structures, within multi-well plates. Similarly, high throughput cell culture systems with integrated microfluidics or multi-electrode arrays have also been developed on multi-well or standard microscope slide formats.

Commercial 3D bioprinters capable of printing directly into multi-well plates are available from a number of companies, including the BioAssemblyBot™ bioprinter from Advanced Solutions, Inc. (Louisville, Ky., US), the Regenova® bioprinter from Cyfuse Biomedical K.K. (Tokyo, JP), and the NovoGen MMX™ bioprinter from Invetech, Inc. (Melbourne, AU). These systems use a raster-scanning approach (i.e., "inkjet-like") to fabricate the 3D constructs via extrusion of the biomaterial and, thus, suffer from inherent limitations in scalability, resolution, and material selection.

Highly-specified 3D cell culture microenvironments can be utilized in a broad range of physiological contexts, including in vitro neuronal cultures. The goal of studying isolated neural cultures is to examine and probe a simple in vitro system that can represent physiologically relevant models. Isolated neural cultures are a cornerstone of neuroscience research, yet their utility in reflecting native physiology is limited due to their inherently indeterministic connectivity. Although a large sum of neurophysiological data that details the function of monolayers of neurons is widely available, the conditions used for these cultures vary drastically from the ones present in native tissue. Thus, it is reasonable to assume that the behavior of 2D cultures is not a good representation of the complex system that is the in vivo neural physiology.

Recent work demonstrates that growing neurons in 3D scaffolds with incorporated glia provides drastic morphological and electrophysiological differences in comparison to neural networks grown in 2D cultures. This is attributed to the fact that 3D neural scaffolds better resemble the complex neural environment present in vivo.

In vitro replication of neural circuitry may help elucidate essential parts of the neural milieu and facilitate testing of connectivity models that contribute to higher-level processes. Additionally, as patient-specific induced pluripotent stem cells (iPSCs) are adopted for in vitro disease models, controlling the functional arrangement of neural populations may be critical to recreate normal versus pathological neural circuits. Conventional means for neuronal patterning are often restricted to a 2D context and use substrates that do not reflect native mechanochemical properties. On the other hand, methods to generate soft 3D scaffolds can be costly, time-consuming, or limited to simple geometric features. Given the limitations of current platforms, there is a need to establish a high-throughput means for deterministically controlling and systematically investigating the network dynamics of fundamental neural circuits in more physiologically representative, soft 3D environments.

Engineering a simplified neural circuit with the flexibility for systematically increased complexity provides an attractive model for studying neural wiring and functional connectivity. Current high-density recording and stimulation techniques via surface microelectrode arrays in vitro provide a wealth of information on the state of the network, and the utility of an in vitro model extends also to drug screening given its high throughput nature. Recent innovations in culturing neurons and guiding neural growth offer some control over network connectivity, cell density, and neural phenotypes to achieve some order and simplicity in the network. Notably, the advent of 3D cultures where neurons are grown within hydrogel scaffolds (with thicknesses of at least 10 cell diameters) have served to address the limitations of the 2D model by: 1) maintaining more relevant cell-cell/cell-matrix interactions, 2) protecting neurons from pH changes in culture media, 3) employing a mechanically softer interface that reflects native physiology more so than hard substrates in 2D cultures, and 4) providing high surface area for growth and migration. Thus, 3D constructs are essential to progress in the study of isolated neural networks and the development of physiologically relevant "brain-on-a-chip" systems. Recent advances in this area demonstrate the potential for sustaining neurons in 3D scaffolds for weeks while guiding neural growth in controlled geometric patterns. However, challenges remain in: 1) achieving high spatial resolution and density in recording and stimulation, 2) simplifying costly and laborious fabrication techniques, and 3) producing heterogeneous co-cultures of neurons and glia, which has proven critical for the proper function of neurons.

BRIEF SUMMARY OF THE INVENTION

In an exemplary embodiment, a method and system are provided for rapid generation of polymeric scaffolds with highly specified 3D geometries. The inventive biofabrication method is referred to herein as "Layerless 3D Printing via Dynamic Optical Projection", or "L3PDOP". The inventive L3PDOP 3D printing system and method can receive an input comprising a 3D computer-generated model and from that model generate the structure in a variety of photopolymerizable materials with high resolution. The inventive 3D printing system uses a dynamically controlled DMD (digital micromirror device) to reflect a high resolution pattern of UV light onto a photopolymerizable substrate. Integration with custom computer software allows for the simultaneous and continuous control of the projected image and the linear stage that controls the position of the substrate in relation to the focal plane of projected light. Due to the continuous movement of the stage, the fabricated 3D structures have smooth (i.e., layerless) contours in the Z (vertical) direction. By controlling the composition of the pre-polymer solution, for example, by inclusion of naturally-derived and/or synthetic biomaterials, bioactive molecules, heterogeneous cell populations, 3D structures that mimic native tissue environments can be created within seconds. Additionally, rapid control of the micromirror array provides for micron and sub-micron level changes in local material properties (such as porosity and material stiffness) via spatiotemporal patterning of transient UV exposure throughout the polymer.

According to embodiments of the invention, a system and method for 3D microfabrication are provided by projecting light capable of initiating photopolymerization toward a spatial light modulator that modulates light responsive to digital masks corresponding to layers of the structure. Projection optics focus the modulated light onto an optical plane within a photopolymerizable material supported on a stage. A computer controller causes the spatial light modulator to project a sequence of images corresponding to the digital masks while coordinating movement of the stage to move a position of the optical plane within the photopolymerizable material to sequentially project each image of the sequence to generate the structure by progressively photopolymerizing the photopolymerizable material.

The inventive method and system provide a novel stereolithographic approach via dynamic continuous control of a micromirror array (DMD) along with a linear stage. Specifically, the device allows for an improvement over the state of the art due to its speed, scalability, and layerless Z resolution. By providing layerless resolution, the fabricated structures do not exhibit the planar artifacts produced using traditional layer-by-layer fabrication approaches that involve discrete movement of the linear stage to a new height position. Furthermore, the inventive L3PDOP 3D printing platform provides for rapid and scalable fabrication of highly-specified biomimetic structures. This approach provides capability in terms of speed and scalability that cannot be well-achieved using existing technologies that employ raster-based printing approaches or soft lithography techniques. Additionally, as the L3PDOP system can accept virtually any set of high-detail images, this platform provides a method for generating models with specificity not only in terms of cell type but also whole tissue morphology. The flexibility of the platform allows for the modular addition and subsequent decoupling of various components of a complex 3D construct, providing a means to determine the individual contributions of material type, co-culture populations, spatial cell arrangements, and biomimetic geometries. Modes of operation for the apparatus include 3D microscale bioprinting of biological substrates via dynamic stereolithography, and optogenetic control of neurons with high spatiotemporal resolution, along with accompanying integrated capabilities for simultaneous electrophysiology and fluorescence imaging. Stereolithographic 3D bioprinting allows for photopolymerization of multiple biocompatible materials (e.g., PEGDA, MeHA, GelMA) and facilitates cell encapsulation within these structures. Additionally, these materials—along with their incorporated cell types—can be used heterogeneously in the same scaffold to provide 3D patterned co-culture substrates, thus facilitating the study of interactions among multiple cell phenotypes, e.g., neuronal/glial interactions.

As individual pixels of the micromirror array can be switched on and off rapidly throughout the fabrication process, highly localized (e.g., submicron) changes in polymer structure in terms of porosity or material stiffness can be achieved through the spatiotemporal control of pixel-level UV exposure. This platform addresses limitations in the field by allowing simultaneous control over scaffold composition, microstructure, and larger scale 3D geometry as well as providing improvements in speed and scalability.

In one aspect of the invention, a pre-polymer solution containing free-radical absorbers to inhibit light-activated free-radical polymerization/cross-linking is used to limit the curing depth. A surface treatment may be applied to the window, which may be composed of sapphire or glass (or any other sufficiently rigid optically-transparent material), to prevent polymerization/adhesion of the structure onto the immersed window. This is in contrast to the Carbon3D approach, with printing using the inventive platform occurring directly onto the floor of the bath as opposed to on an immersed probe. This allows the rapid printing of 3D structures within each well of a multi-well plate as the plate is translated within X-Y axes to move from well to well. By not relying on a single large bath immersion, each well can contain a different polymer composition and may ultimately hold a different 3D structure.

In another aspect of the invention, the method and device are operable for recording network activity across multiple domains. For example: 1) multi-electrode arrays (MEAs)—on which the 3D neuron network structures (or any electrically active cell type) are printed—allow orthogonal recording of electrical activity concurrent with optogenetic stimulation; and 2) fluorescent imaging of voltage-sensitive dyes and proteins, which provides enhanced single-cell resolution of network activity, can be simultaneously performed by employing the same or similar light source utilized for bioprinting.

In one application of the inventive 3D printing method and system, a brain-on-a-chip is generated by integrating 3D heterogeneous neural cultures, optogenetics-enabled high-resolution stimulation, and parallel electrical and image-based recording of neural activity. The fabrication methods utilized in this platform offer control over both the topographical complexity and the cellular and material composition of the neural environment, thereby allowing for the potential for systematically-controlled increases in complexity.

In one aspect of the invention, a system for 3D microfabrication of a structure, includes a light source configured for projecting light within an optical path, the light source emitting light at a wavelength configured for initiating photopolymerization; a spatial light modulator disposed within the optical path and configured for modulating light from the light source responsive to a set of digital masks corresponding to layers of the structure; projection optics configured to focus the modulated light to an optical plane; a stage configured to support a substrate in contact with a photopolymerizable material within the optical plane, wherein the stage is configured for movement along at least one axis; and a computer processor operable for: controlling the spatial light modulator to project a sequence of images corresponding to the set of digital masks; and coordinating movement of the stage to move a position of the optical plane within the photopolymerizable material to sequentially project each image of the sequence to generate the structure by progressively photopolymerizing the photopolymerizable material along the at least one axis. In some embodiments, the spatial light modulator may be a digital micromirror device. The photopolymerizable material may be a pre-polymer solution contained within a container, and the system further comprises a transparent window configured for contact with the pre-polymer solution, where an interface between the window and the pre-polymer solution is substantially coincident with the optical plane. In one embodiment, the stage is moved toward the optical plane so that successive layers of the structure are projected through previously polymerized layers. In another embodiment, the window is sealed to an end of a tube for immersion in the pre-polymer solution and the stage is moved away from the optical plane so that successive layers are polymerized on top of previously polymerized layers. The window may be treated to inhibit adhesion of the photopolymerizable material and may be formed from a material selected from the group consisting of silica, sapphire, polydimethysiloxane (PDMS), transparent ceramic, and transparent plastic. In some embodiments, the container comprises a well within a multi-well plate. The multi-well plate may comprise a plurality of containers, where at least of portion of the containers contain different pre-polymer solutions.

In other embodiments, the substrate comprises an electrode or a multi-electrode array. In some of these embodiments, the electrode or multi-electrode array is contained within a well within a multi-well plate, which itself may comprise a plurality of containers, where at least of portion of the containers contain different types and numbers and spatial configurations of electrodes. In these embodiments, the photopolymerizable material may be a conductive polymer and at least a portion of the sequence of images corresponds to interconnecting structures aligned with one or more electrodes.

The photopolymerizable material may be a photo-crosslinkable hydrogel selected from the group consisting of gelatin methacrylate [GelMA], methacrylated hyaluronic acid [MeHA] and polyethylene glycol diacrylate [PEGDA].

The system may include at least one second light source disposed within the optical path, the at least one second light source emitting light at one or more wavelengths configured to stimulate at least one photo-active biological material. The system may also include an image acquisition device disposed within the optical path.

In some embodiments, at least a portion of the digital masks may be configured to cause the spatial light modulator to generate subpatterns within selected layers of the structure.

In another aspect of the invention, a method for 3D microfabrication of a structure includes controlling a spatial light modulator to project a sequence of patterns of light from at least one light source having an optical path and emitting at a wavelength configured to initiate photopolymerization onto a photopolymerizable substrate, wherein the substrate is mounted on a stage configured for movement along at least one axis, and wherein the sequence of patterns corresponds to layers of the structure; and simultaneously and continuously controlling the sequence of patterns and the stage movement to generate the structure by progressively photopolymerizing the photopolymerizable substrate along the at least one axis. The sequence of patterns is preferably generated by a set of digital masks communicated from a computer controller to the spatial light modulator.

In some embodiments, the photopolymerizable substrate comprises a pre-polymer solution contained within a container, and the method further comprises positioning a transparent window in contact with the pre-polymer solution to define the polymerization plane. In one embodiment, the stage is moved toward the photopolymerization plane so that successive layers of the structure are projected through previously polymerized layers. In another embodiment, the window is sealed to an end of a tube for immersion in the pre-polymer solution and the stage is moved away from the polymerization plane so that successive layers are polymerized on top of previously polymerized layers. The different stage movement directions may be combined, with some structures built from a combination of top-down and bottom-up stage movements.

In some embodiments, the container may be a well within a multi-well plate that may include a plurality of containers, wherein at least of portion of the plurality of containers contain different pre-polymer solutions. In other embodiments the substrate may be an electrode or a multi-electrode array. The photopolymerizable substrate may be a conductive polymer and at least a portion of the sequence of patterns corresponds to interconnecting structures aligned with one or more electrodes.

The photopolymerizable substrate may be a photo-cross-linkable hydrogel selected from the group consisting of gelatin methacrylate [GelMA], methacrylated hyaluronic acid [MeHA] and polyethylene glycol diacrylate [PEGDA].

BRIEF DESCRIPTION OF THE DRAWINGS

FIG. 2 shows an exemplary process flow for generating a cell-laden 3D scaffold using the L3PDOP printing method.

FIGS. 4A-4C are a series of confocal fluorescent micrographs showing cell interactions with the manufactured scaffolds.

FIGS. 8A-8C illustrate an alternative embodiment of the inventive 3D printing platform, where FIG. 8A diagrammatically illustrates the printing of polymer scaffolds using different pre-polymers in a multi-well plate, FIG. 8B provides a detail view of the optical assembly of FIG. 8A, and FIG. 8C diagrammatically illustrates an exemplary process flow for layerless printing of a 3D scaffold.

FIGS. 9A and 9B illustrate examples of using of the alternative printing platform of FIGS. 8A-8C, where FIG. 9A is a screenshot of the CAD software used to design and render two different 3D models, and FIG. 9B provides micrographs of the resulting printed hydrogels.

FIGS. 13A-13C show a CAD design of a rat brain and possible subpatterning arrangements at different "layers" or "slices", respectively.

FIGS. 23A and 23B show an exemplary training sequence with time; FIG. 23C illustrates a diagram of an MEA.

DETAILED DESCRIPTION OF EXEMPLARY EMBODIMENTS

Figure 1A:
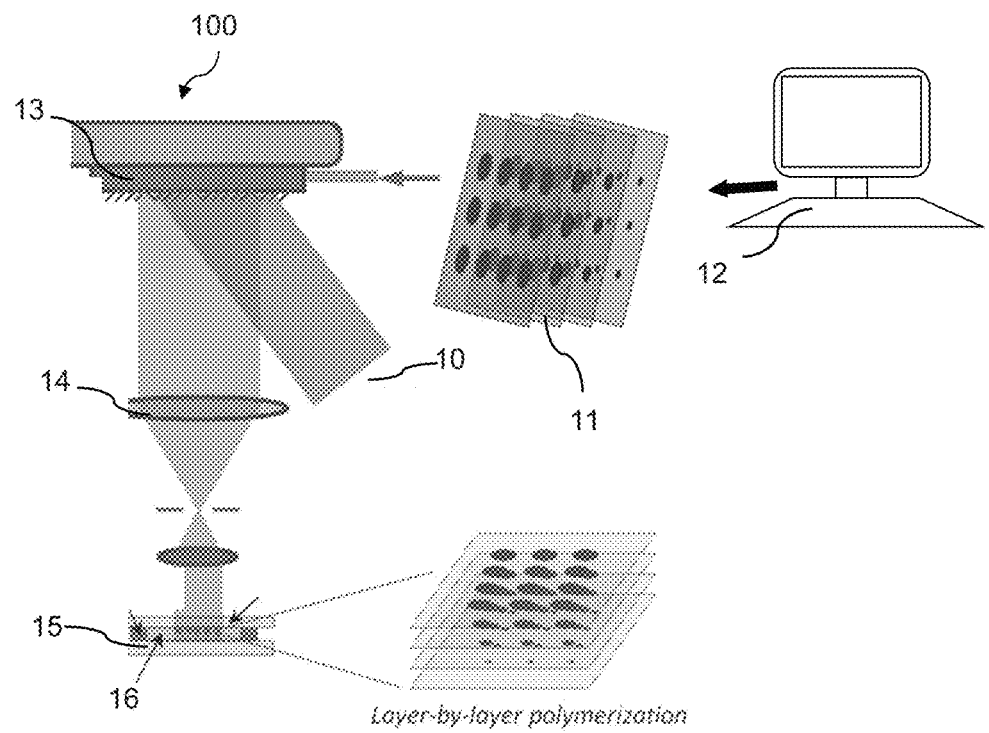
FIG. 1A is a schematic diagram of an embodiment of the L3PDOP 3D printing system.

The basic elements of a L3PDOP 3D printing platform 100 according to an exemplary embodiment of the invention are illustrated in FIG. 1A: a UV light source 10, a computer controller/processor 12, which performs sliced image-flow generation, i.e., "virtual masks" 11, and system synchronization, a digital micromirror device (DMD) chip 13 for optical pattern generation, a projection optics assembly 14, and an multi-axis stage 15 for sample position control. The DMD chip 13, formed from approximately one million micro-mirrors, modulates the UV light and projects an optical pattern generated via computer 12 based on a custom-designed computer-aided design (CAD) model onto the photopolymer solution. The optical pattern is projected through optical lenses 14 and onto the photosensitive biomaterial 16 to fabricate a 3D scaffold. Complex 3D structures are fabricated through a continuous, layer-by-layer polymerization process that is synchronically controlled using a motorized multi-axis stage 15.

An appropriate UV light source 10 for use in the L3PDOP system can be selected from different sources including a laser (CW or pulsed), mercury bulb (arc lamp), and an LED source, which may include an array of LEDs emitting at one wavelength or across a range of UV wavelengths. In an exemplary embodiment, a pulse mode-locked femtosecond laser may be used. The light source 10 may include controllable parameters, responsive to the computer controller/processor 12, including intensity, iris, aperture, exposure time, shutter, and wavelength. Selection of appropriate operating parameter will depend on the materials used and the desired characteristics of the scaffold and will be within the level of skill in the art.

As an alternative to the DMD chip, a galvanometer optical scanner or a polygon scanning mirror, may be used. Both of these technologies, which are commercially available, are known in their application to high speed scanning confocal microscopy. Selection of an appropriate scanning mechanism for use in conjunction with the inventive system and method will be within the level of skill in the art.

Figure 1B:
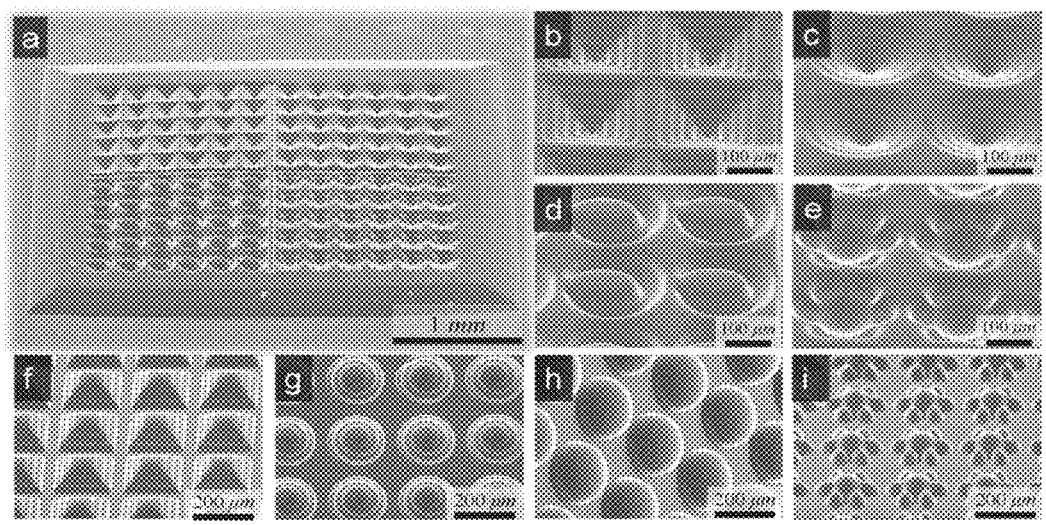
FIG. 1B is a set of SEM images of complex geometries created using an L3PDOP printer.

Examples of structures generated using the inventive printing system are shown in FIG. 1B, which is a series of scanning electron microscope (SEM) images of PEG microwells with complex geometries including: (b) stepwise, (c) spiral, (d) embryo-like, and (e) flower-like. FIG. 1B(a) is a combination of arrays of the structures shown in (b)-(e). FIG. 1B images (f)-(i) are the inverse of the microwells of (b)-(e), demonstrating the versatility of the L3PDOP printing method.

The masks 11 are similar in form to a set of "PowerPoint-like" slides, and can be dynamically altered as per the CAD model to design and fabricate a wide variety of 3D features. A significant advantage of the inventive system is that it does not require the use of organic solvents that may otherwise compromise the biocompatibility of the scaffold material. The inventive 3D printing technology is ideal for high-throughput fabrication and is easily scalable, a necessary requirement for generating high-volume screening platforms.

FIGS. 2A-2C illustrate an exemplary process sequence for fabricating a 3D scaffold using the L3PDOP printing system 100 and method. As in the system shown in FIG. 1A, the basic elements of the system 100 are a UV light source 110, a computer controller/processor (not shown), which performs sliced image-flow generation, i.e., "virtual masks" 111, a digital micromirror device (DMD) chip 113 for optical pattern generation, a projection optics assembly 114, and an multi-axis stage 115 for sample position control. Cells in a macromer solution 124 are placed in a chamber 126 covered by a transparent coverslip 128. In an exemplary embodiment, the coverslip 128 is methacrylated glass. Polymerization of the 3D scaffold 130a begins at the coverslip surface 128, where the reflected UV image corresponding to Mask 1.0 from the DMD array 113 is focused at imaging/polymerization plane 120 in step 1 shown in FIG. 2A. Starting from the base or bottom portion of the scaffold 130a, which is cross-linked to the coverslip 128, the complete structure is fabricated in one continuous process. Mask 1.0 represents the basic shape of a base portion 130a, which can be varied gradually in dimension, e.g., with multiple masks, up to Mask 1.0.n, being projected on the DMD, as the structure builds to generate sloped or curved edges. The projection mask on the DMD 113 shifts to Mask 2.0-2.0.n as the servo-controlled platform 115 translates up to move the fabricated base portion 130a past the polymerization plane 120 (step (2) shown in FIG. 2B) and to bring the next portion of the chamber 126 and macromer solution 124 into the polymerization plan 120 to form the second part of the scaffold 130b. As with the base, the dimensions of the mask may be varied to create curved and slopes edges in the sample shape(s). The top of the scaffold 130c is reached in step (3) as determined by Mask 3.0-3.0.n (FIG. 2c). Through this sequence, the cells can be encapsulated in a user-defined 3D structure. FIG. 2D diagrammatically illustrates a top view (upper) and side view (lower) of the exemplary 3D scaffold resulting from the steps shown in FIGS. 2A-2C.

In one embodiment of the invention, one or more one image acquisition devices may be included within the optical path to allow incident light or the projected image to be transformed through the projection optics assembly to allow a focal plane of the image to be coincident with the focal plane of said image acquisition device. The image acquisition device may be used to capture the incident light, the projected image, or a pattern of light emitted, reflected, transmitted, or otherwise transformed by said substrate. Appropriate image acquisition devices include CMOS cameras, CCD cameras or microscopes, e.g., fluorescent microscopes.

A prototype of the L3PDOP micro-stereolithography ("µSL") system was constructed to fabricate 3D scaffolds such as a tube, conduit, log-pile, and vascular-like structure. The system has been used to create structures from various biopolymers including polyethylene glycol diacrylate (PEGDA, functionalized with fibronectin for cell adhesion), methacrylated hyaluronic acid (MeHA), and gelatin methacrylate (GelMA) for the 3D scaffolds. These precisely engineered biomimetic scaffolds offer a unique platform for the investigation of cell interaction with micro-environments. Encapsulated cells demonstrate good cell viability across all geometries both on the scaffold surface and internal to the structures. Cells respond to geometric cues individually as well as collectively throughout the larger-scale patterns.

Figure 3:
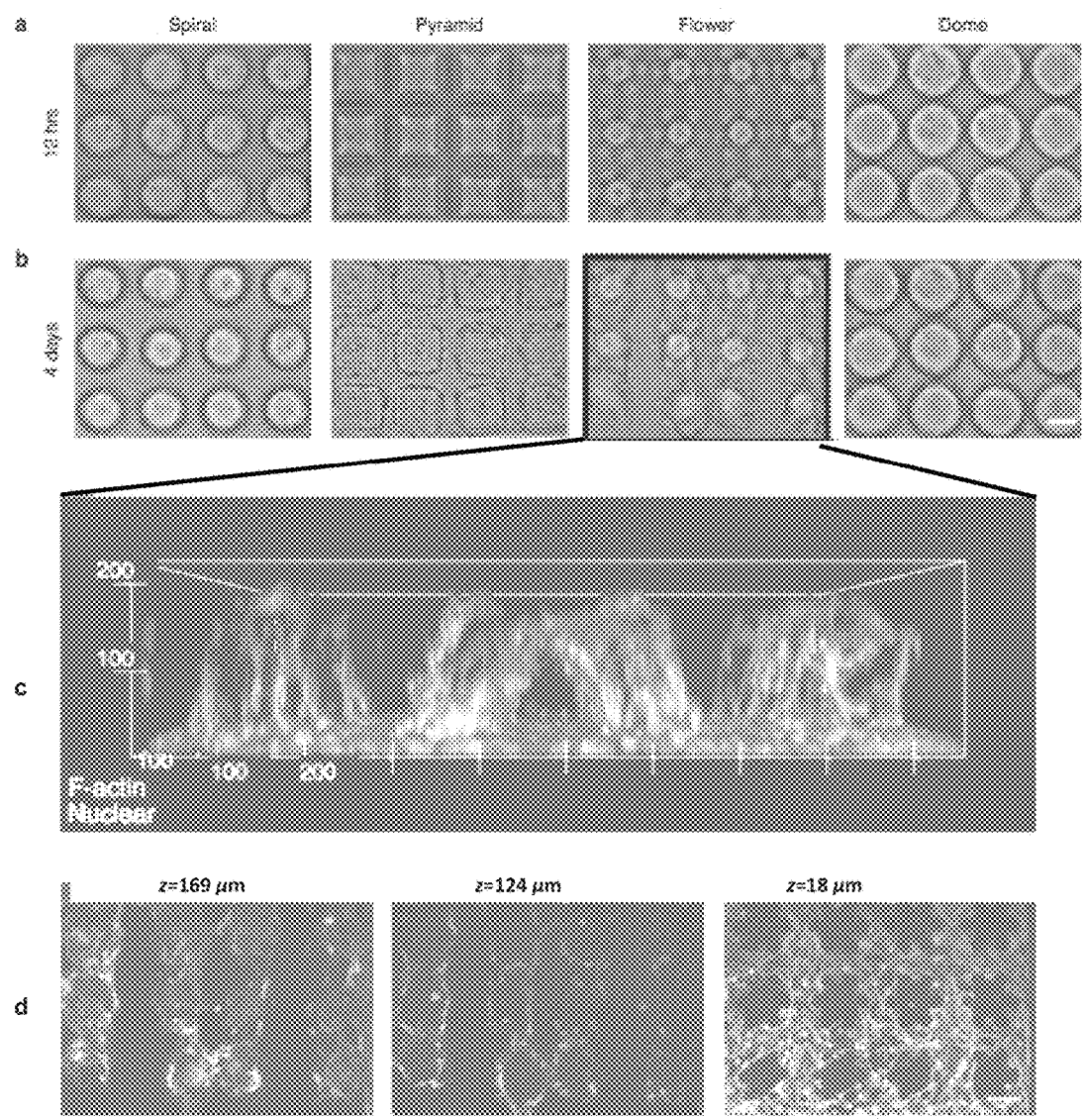
FIG. 3 is a series of brightfield and confocal fluorescent micrographs showing scaffolds made using an L3PDOP printer and cell interactions with the scaffolds.

FIG. 3 provides micrographs of examples of cellular response to complex 3D geometric cues, demonstrating dynamic interaction with the scaffolds to remodel the position and shape of the structures. Upper panel (a) shows GelMA (gelatin methacrylate) scaffolds with encapsulated NIH/3T3 cells at 12 hrs post-fabrication. Second panel (b) reveals deformation of the structures as observed four days post-encapsulation. Panel (c) is a 3D reconstruction of confocal fluorescence micrographs indicating height-dependent deformation of the scaffold as mediated by cell-cell interactions across two flower structures (third image of panel (b). Cells were stained for F-actin (red) and nuclei (blue). In Panel (d), individual Z sections of the same flower structures as shown in panel (c) demonstrate height-dependent deformation when progressing up from the floor to the top of the structures. All scale bars are 100 µm.

Figure 4C:
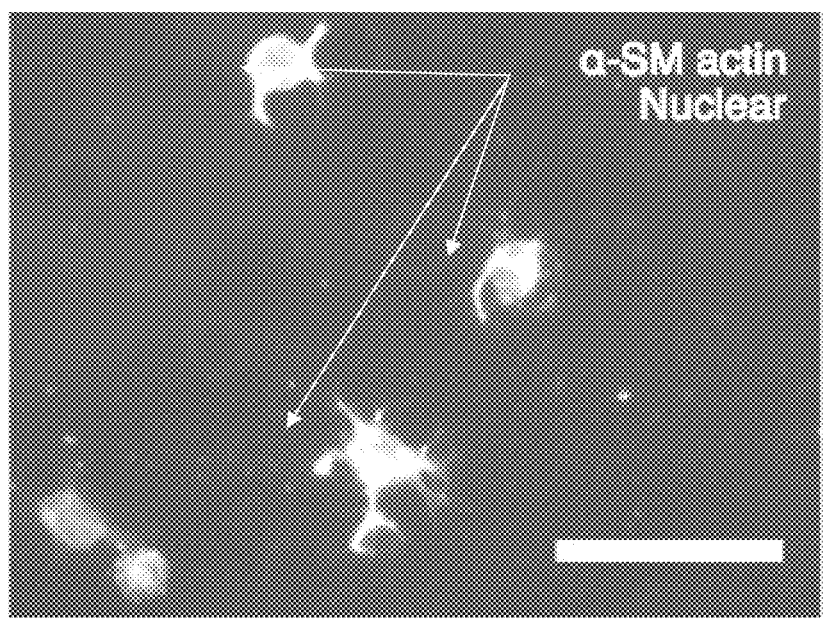

FIGS. 4A-4C provide micrographs of cells that remain encapsulated within the GelMA scaffolds, exhibiting 3D cell spreading while maintaining active cell-material interactions. Confocal fluorescence micrographs reconstructed in 3D (FIG. 4A) and viewed at various Z planes (FIG. 4B) throughout the scaffold reveal NIH/3T3 fibroblasts on the scaffold surface displaying morphology different from cells internal to the structures. In FIG. 4B, cells that remain embedded within the GelMA scaffold at 4 days post-encapsulation exhibit extension of pseudopodia preferentially towards the surface of the encapsulating structure. Cells were stained for F-actin (red) and nuclei (blue). In FIG. 4C, 10T1/2 cells encapsulated within GelMA scaffolds express a smooth muscle cell phenotype, as shown via staining for α-SM actin (green), and maintain cell-material interactions at 8 days post-encapsulation as indicated by 3D projections of pseudopodia. All scale bars are 50 µm.

The microfabrication of highly complex 3D biomimetic structures that feature cellular and biomaterial components that recreate native physiology can yield myriad applications in both clinical settings as well as within basic research and development. Providing tissue constructs based on patient specific anatomy at a scalable and high throughput level can address a rapidly growing market in regenerative medicine. Complex scaffold geometries can be utilized with cell seeding and/or cell encapsulation to provide optimal conditions to guide the differentiation of stem cells and/or maintain their pluripotency. Commercial services can be established to provide built-to-order high throughput cellularized scaffold arrays to investigate cell responses within complex 3D geometries and interfaces. The commercial application can be more generalized as well to provide micron-resolution components within seconds using any photopolymerizable material. This provides a significant improvement to current rapid prototyping systems that still find limitations in fabrication time, feature resolution, and layer artifacts.

Figure 5:
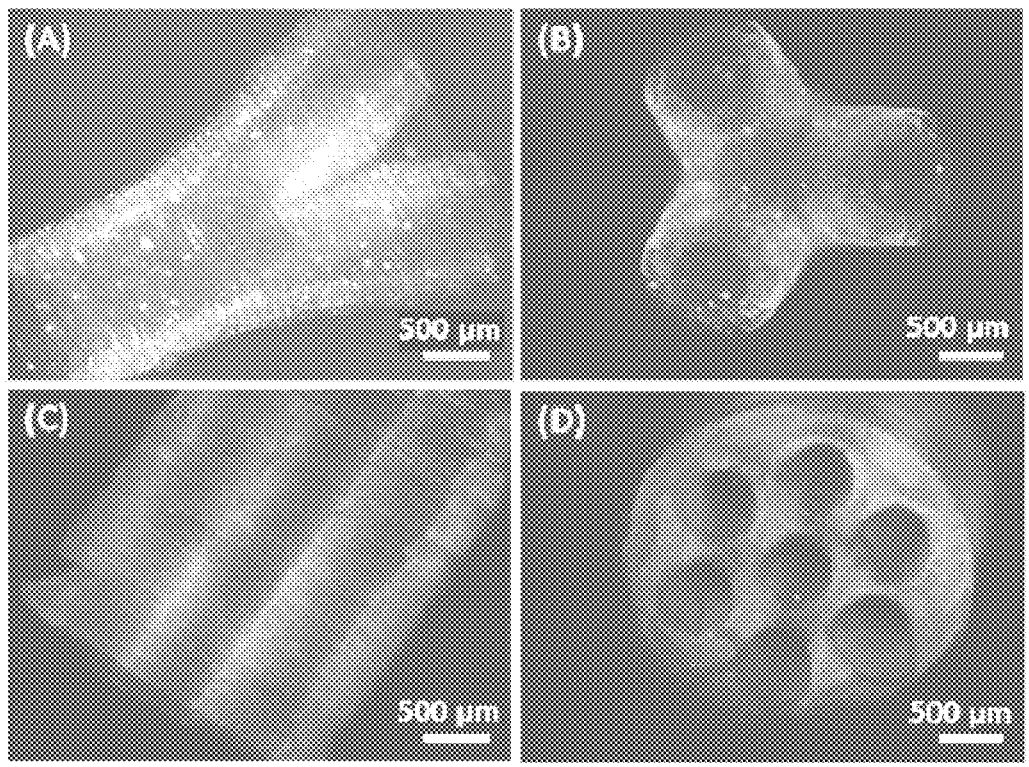
FIG. 5 is a set of fluorescence micrographs (A-D) showing various 3D scaffolds.
Figure 6A:
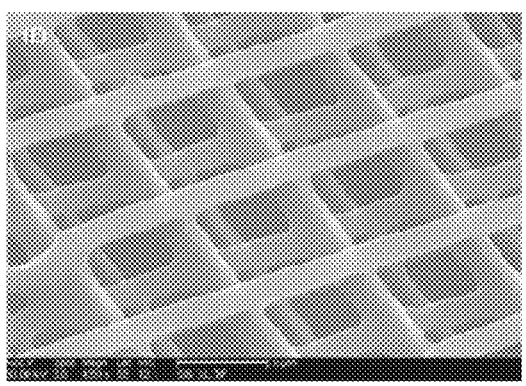
FIG. 6A is a scanning electron micrograph of a log-pile scaffold.
Figure 6B:
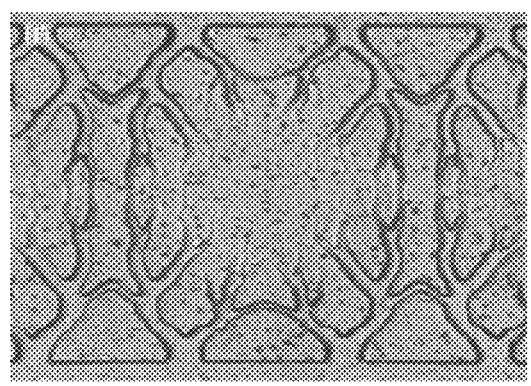
FIG. 6B is an optical micrograph of a vascular microstructure using an implementation of the inventive printing platform.

FIG. 5 is a set of fluorescence micrographs (A-D) showing examples of various 3D scaffolds constructed from hyaluronic acid using the inventive 3D printing platform. FIG. 6A is a scanning electron micrograph of a log-pile scaffold and FIG. 6B is an optical micrograph of a vascular microstructure made of GelMA using the inventive L3PDOP printing platform.

The CAD model for generating masks for L3PDOP printing of the 3D scaffold generally consists of a series of slices of digital images. The images may also be derived from MRI or CT scans. With the control computer and appropriate software, the images are automatically and continuously loaded one-by-one into the DMD chip and then projected into the photo-polymerizable materials to form 3D structures through a digital, continuous polymerization process. The flexibility of the platform allows for the modular addition and subsequent decoupling of various components of a complex 3D construct, providing a means to determine the individual contributions of material type, co-culture populations, spatial cell arrangements, and biomimetic geometries. As individual pixels of the micromirror array can be switched on and off rapidly throughout the fabrication process, highly localized (e.g., submicron) changes in polymer structure in terms of porosity or material stiffness can be achieved through the spatiotemporal control of pixel-level UV exposure.

The instrumentation for the inventive system (i.e., DMD array, UV lamp, linear stage) may be controlled via software built in Visual C++ or Go (golang.org) or similar object-oriented programming languages. The software may offer a graphical user interface, which can be realized 1) in a locally executed and controlled standalone computer application or 2) as a web-based application framework hosted by a server connected to the instrumentation and accessed by remote clients via the Internet, that provides integrated control over the parameters of each component, allowing the user to specify the image sequence projected, the exposure time per image, the intensity (iris setting) of the UV source, the initial stage position, and the total height of the structure. In addition to image sequences, which may be imported as bitmap (.BMP) or .PNG (or equivalent) files, the software may also accept text-based data files (.DAT files) that are formatted in a custom syntax that specifies the mirror state (ON vs. OFF) of each micromirror in the array for each voxel (i.e., x,y,z coordinate) of a 3D structure. Thereby, 3D structures can be specified not only via a sequence of bitmap images but also via an algorithmic/mathematical function. Furthermore, capability may be included to convert a topographical bitmap representation of a 3D structure into a .DAT file featuring the proper syntax. Additionally, the software can import any other standardized format that specifies 3D structure information, e.g., STL files. Finally, the software would preferably control the stage along the X and Y axes, which can provide the capability of high-throughput, batch fabrication of multiple geometries in a large array format.

To match the mechanical property of biological tissue, naturally-derived gelatin methacrylate (GelMA) hydrogel may be used as the base material. (See, e.g., J. W. Nichol, et al., "Cell-laden microengineered gelatin methacrylate hydrogels. *Biomaterials* 31, 5536-5544 (2010).) The addition of methacrylate moieties to the side groups of natural gelatin enables photopolymerization or photocrosslinking of the hydrogel, allowing intricate structures supporting cell adhesion and growth to be engineered.

In one experiment to synthesize GelMA, porcine skin gelatin (Sigma Aldrich) is mixed at 10% (w/v) into phosphate buffered saline (PBS; Gibco) and stirred at 60° C. until fully dissolved. Methacrylic anhydride (MA; Sigma) was added to the solution at a rate of 0.5 ml/min until a concentration of 8% (v/v) of MA was obtained in the gelatin solution. The solution was stirred for 1 hour at 50° C., followed by a 2× dilution with warm PBS and dialyzed against distilled water using 12-14 kDa cutoff dialysis tubing (Spectrum Laboratories) for one week at 40° C. to remove the unreacted groups from the solution. The GelMA solution is frozen overnight at −80° C. and lyophilized in a freeze dryer (Labonco) for one week. Freeze dried GelMA foam is stored at −80° C. until further usage. To prepare the hydrogel prepolymer, freeze dried GelMA macromer was mixed into PBS at a 10% or 15% concentration and stirred at 60° C. until fully dissolved. Photoinitiator (1% (w/v), Irgacure 2959, CIBA Specialty Chemicals), UV absorber (0.1% (w/v) HMBS, (2-hydroxy-4-methoxy-benzphenone-5-sulfonic acid), Sigma) and free radical quencher (0.01% (w/v), TEMPO, Sigma) was added to the solution to allow for photopolymerization and provide efficient cure depth and optimal pattern resolution. To evaluate the degree of curing, the FTIR spectrum of the GelMA macromers was measured for comparison to crosslinked GelMA to assess the extent of spectrum change.

The inventive biofabrication method may be used to create a biomimetic three-layer spiral line scaffold. The scaffold structural parameters (spacing, height, etc.) can be optimized to facilitate the delivery of nutrients, oxygen, and other factors. Different combinations of: (a) GelMA solution concentrations, (b) UV exposure times, and (c) UV intensities may be used to control the scaffold structural parameters. Various biochemical factors (drugs/growth factors or biomolecules) can also be incorporated along with 3D biostructural arrangement. Such a functional scaffold allows temporal release of the entrapped biomolecules to facilitate prolonged and sequential signaling to optimize cell function. 3D biomimetic scaffolds may be fabricated either on a glass slide or a PDMS substrate. A stretchable PDMS chip may be used for evaluation of how mechanical stress affects the scaffold and the encapsulated biological material.

To reduce the potential for UV damage, a recently discovered photoinitiator, lithium phenyl-2,4,6-trimethylbenzoylphosphinate (LAP) may be used. (See, e.g., B. D. Fairbanks, et al., "Photoinitiated polymerization of PEG-diacrylate with lithium phenyl-2,4,6-trimethylbenzoylphosphinate: polymerization rate and cytocompatibility", *Biomaterials* 30, 6702-6707 (2009).) LAP offers greater water solubility, higher polymerization efficiency with a 365 nm light source, and minimal cytotoxicity. Moreover, LAP has significant absorbance above 400 nm which allows efficient polymerization using visible light. In other implementations, photoinitiators with absorbances across other wavelengths in the visible spectrum may be employed.

Tensile tests can be performed on the 3D spiral scaffolds to determine failure strain, ultimate tensile strength, and strain energy density. Each biological scaffold (2 cm×1 cm×0.5 cm) may be placed within an Instron 5542 machine, fitted with grips and a 50 N load cells. A mechanical test of three cycles of strain in the range of 0.05 and 0.2 may be applied to the samples with a strain rate of 2 mm/min until failure. The slow rates may be chosen to minimize viscoelastic effects. Results of these measurements may be compared with natural tissues from literature and guide the design of the scaffolds.

Since GelMA is derived from mammalian extracellular matrix (ECM), this biomaterial should exhibit low toxicity and good biocompatibility. However, if the GelMA scaffolds do not achieve the desired mechanical properties for the intended application, hyaluronic acid (HA), a naturally derived non-sulfated glycosaminoglycan and a component of extracellular matrix, can be used in combination with GelMA. Fibroblast can also be incorporated in the same or alternate layers to fabricate multi-cell spatially distributed environments.

An important goal of the inventive printing system and method is to provide for creation of a biomanufacturing platform to develop micro-tissue-on-a-chip with integrated biosensors using, for example, mouse cardiac muscle cells and human induced pluripotent stem cell (hiPSC)-derived cardiac muscle cells. The inventive printing platform allows rapid and scalable fabrication of 3D, highly-specified, biomimetic structures. Additionally, the flexibility of the platform allows for the modular addition and subsequent decoupling of various components of a complex 3D construct, providing a means to determine the individual contributions of material type, spatial cell arrangements, and biomimetic geometry towards recapitulating native tissue physiology. The interaction of cells with their microenvironment—composed of extracellular matrix (ECM), aqueous milieu, soluble factors, and neighboring cells—is fundamental to cellular processes such as migration, proliferation, lineage specificity, and tissue morphogenesis. The integrated sensing capability would allow manipulation of the cellular environment with high precision and visualization of the molecular coordination inside the cells in response to their environmental cues.

Unlike currently-available 3D bioprinters, the dynamic optical projection printer according to embodiments of the invention (i.e., the L3PDOP printer) allows for rasterless, one-shot, within-well printing of mechanically soft biomaterial hydrogels with fully-defined complex 3D geometries at near nanoscale resolution. The printing process for a single well can be completed in 15 to 60 seconds for most material types and geometries (with total printed scaffold dimensions of 3 mm×5 mm×1 mm), allowing for printing of a complete 24-well plate within 5 to 15 minutes. Furthermore, each well within the plate can be pre-filled with a polymerizable solution of unique material composition and/or concentration, independent of the geometry to be fabricated. By multiplexing these various parameters across different wells within a culture plate, high throughput 3D cell screening platforms for drug discovery, clinical diagnostics, and basic life sciences research can be manufactured on-demand with custom specification at efficient time scales.

In an embodiment of the inventive printing platform, a tool is created for studying isolated 3D neural networks using stereolithography that allows for fine control over the composition and structure of the 3D neural environment while enabling high resolution stimulation and recording. The utility of this method enables systematic control over the complexity of the neural network and facilitates investigation into the intricate interplay between the neural environment and function. Finally, recent work comparing the neural physiology of 3D cultures to 2D cultures has shown that 3D cultures exhibit complex firing patterns with significant reduction in synchronized activity similar to those found in in vivo networks and in contrast to activity exhibited by 2D cultures. These findings indicate that a classic and well-studied behavior of isolated neural networks can be completely altered in a 3D environment. Thus, the inventive platform represents a significant advancement in the current understanding of the neural computational aspect of isolated neural networks and subsequently their utility for studying the nervous system. These advancements impact fundamental neuroscience research into normal and pathological neural states, while also facilitating the clinical translation of neuroscience network models by providing disease models for accelerating the progress and dramatically reducing the cost of drug discovery for neurodegenerative and psychiatric ailments that afflict millions of individuals.

In one embodiment of the 3D printing platform, a within-well high-throughput printing method is performed as depicted in FIGS. 8A-8C. In this method, in contrast to the "inverted" approach illustrated in and described above with reference to FIGS. 2A-2C, the pre-polymer solution is not isolated completely within the target substrate. Instead, the image is projected such that it is in focus at the distal end of the optical assembly 82 (in this embodiment, focusing lens 88, collimating lens 89, optical tube 87, and window 91), where window 91 (formed from a transparent material such as sapphire, glass, PDMS or other appropriate material) forms a hermetic seal with optical tube 87 so that the window 91 can be immersed within a well 80*a* (as shown) of multi-well plate 80 containing the pre-polymer. For illustration purposes only, multi-well plate 80 is shown with wells 80*a*-80*x*, however, any number of wells may be used. In addition, while two different pre-polymers are labeled in the figure ("Pre-polymer A" and "Pre-polymer B"), a variety of different combinations of pre-polymers may be used to achieve the desired properties within the scaffold, as will be described further below. By positioning the plate 80 up or down relative to the window 91, the volume of pre-polymer and the height of the current printing layer are controlled. Importantly, the window 91 serves to eliminate the formation of a meniscus at the printing interface 90, which could otherwise distort the projected image.

Referring to FIG. 8C, which diagrammatically illustrates "snapshots" of the printing process at times $t_1$, $t_2$ and $t_3$, as the substrate/stage 92 supporting plate 80 and its wells is pulled away from the stationary window 91, fresh pre-polymer solution is drawn into the widening gap via capillary action. This process occurs in a continuous fashion as the stage 92 is translated smoothly across the desired height of the scaffold 86 and results in the most recently printed layer being closest to the printing interface 90, thus defining the "polymerization plane". While described in the terms of "layers", the printing process is actually continuous, such that the layers can also be thought of as "slices" through a continuous structure. The left hand portion of FIG. 8C diagrammatically shows the location of the polymerization plane $z_1$ at time $t_1$, when "layer 50" is printed. The inset corresponding to time $t_1$/layer 50 shows the current digital mask projected from the DMD 84. The center portion of FIG. 8C shows the location of the polymerization plane $z_2$ at time $t_2$, at which time "layer 100" is printed. The inset corresponding to time $t_2$ shows the current digital mask projected from the DMD 84. The right hand portion of FIG. 8C shows the location of the polymerization plane $z_3$ at time $t_3$, at which time "layer 161" is printed. The inset corresponding to time $t_3$ shows the current digital mask projected from the DMD.

Under this printing scheme, the projected light is not transmitted through previously printed layers to print subsequent layers as is done in the "inverted" method described above. This approach allows for printing of much taller structures in addition to the creation of structures with fully enclosed features. This contrasts with attempts to print enclosed cavities or channels using the "inverted" method, which often lead to undesired polymerization in these "void" areas due to the light necessarily passing through these regions to print subsequent layers. Nonetheless the "inverted" method can provide added utility when combined with this immersion-based approach, as one method can be used to fabricate a subcomponent of the complete scaffold using one type of material while the other method can be used subsequently to print different materials within the same scaffold.

Initial results using the non-inverted approach are shown in FIGS. 9A and 9B, where FIG. 9A is a screenshot of the CAD software used to design and render two different 3D models—an open-sided cube (left) and a fenestrated cylinder (right). The printing was carried out on a standard microscope slide with a PDMS gasket placed on top of the slide to define a well to contain the pre-polymer solution. The final printed hydrogels (formed of PEGDA) are shown in FIG. 9B, clearly reflecting the desired morphology determined by the CAD design shown in FIG. 9A.

To ensure preferential adhesion of the cured scaffold to the substrate, as opposed to the optical window, the target glass substrate may be chemically modified to promote cross-linked covalent bonding of the printed structure with the slide or glass-bottomed well plate. In one embodiment, methacrylation is used. In addition, the optical window may also be surface-treated to render it hydrophobic. Issues relating to window adhesion may also be partially mitigated by the continuous fabrication technique itself, which has the advantage that the substrate does not dwell statically at the print interface, which occurs with conventional layer-by-layer printing.

The continuous motion of the stage in synchrony with the dynamic projection mechanism not only allows for "layerless" printing but also offers the ability for hierarchical nanopatterning and/or micropatterning of the printed material. Specifically, subregions within the macroscale structure can be "sub-patterned" with different sequences of spatiotemporal light modulation. As a simple example, a slab or cube structure as in FIGS. 10A and 10B could be printed either by continuous exposure of the same projected square by a steady consistent intensity of light or by intermittently pulsing the intensity of the light. When the light is pulsed or flickered, the flux of photons available to initiate free-radical polymerization at a particular pixel location can be variable. This translates to non-linear differences in polymerization kinetics across adjacent voxels. As the stage is continuously moved while the light is modulated in this fashion, cross-linking or polymerization efficiency can be varied with high spatiotemporal resolution, thus enabling micron or submicron patterning of material properties within the larger simple bulk structure.

Figure 10A:
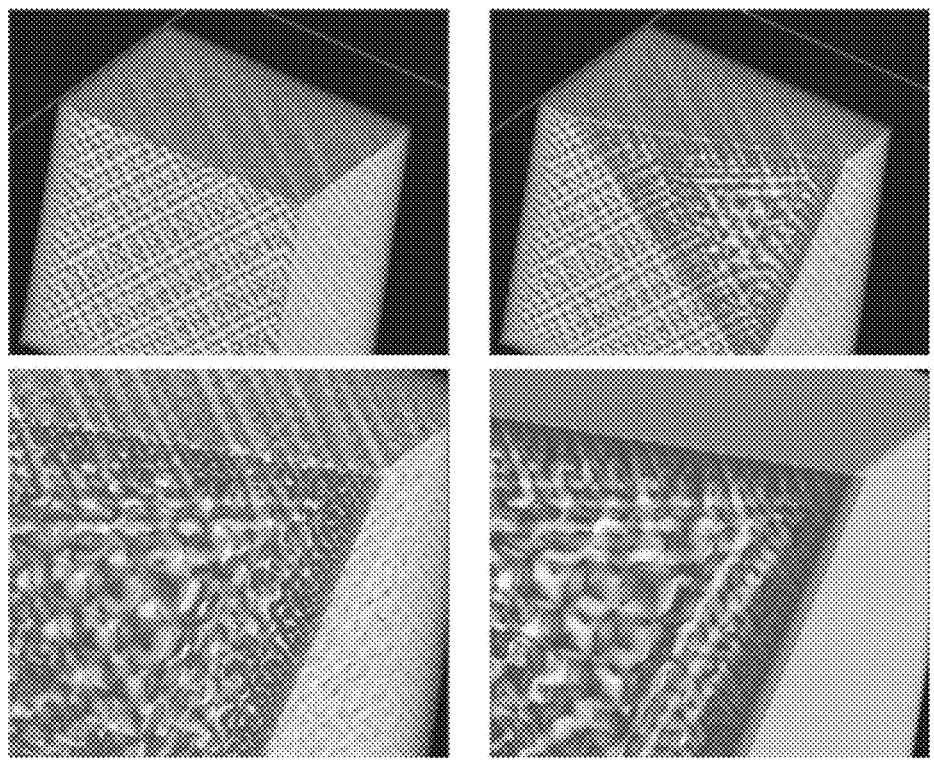
FIG. 10A shows different magnifications of a theoretical rendering of the internal structure of a simple cube as a result of varied subpatterns of light exposure.
Figure 10B:
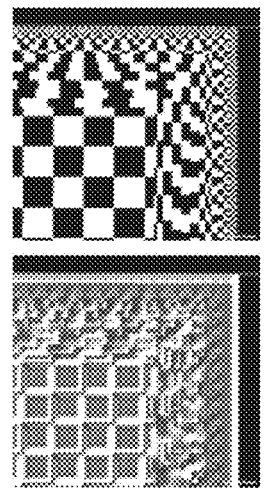
FIG. 10B illustrates examples how an exposure pattern can result in different internal morphologies.
Figure 11:
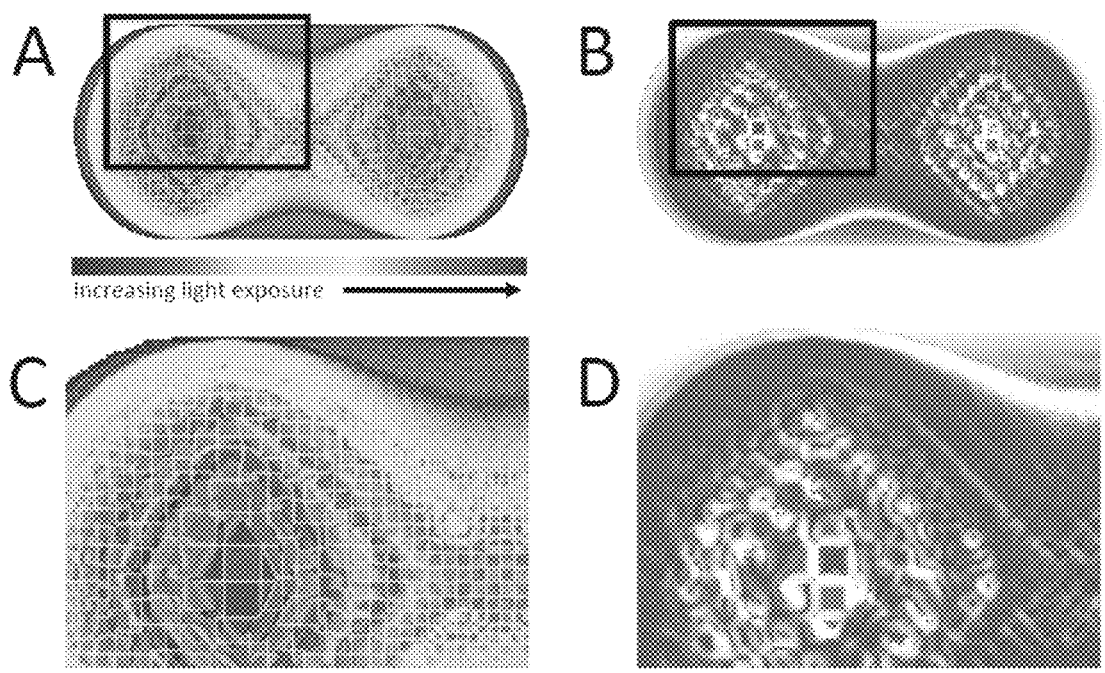
FIG. 11 provides photomicrographs of a patterning algorithm of varying checkerboards applied to a complex shape.
Figure 12:
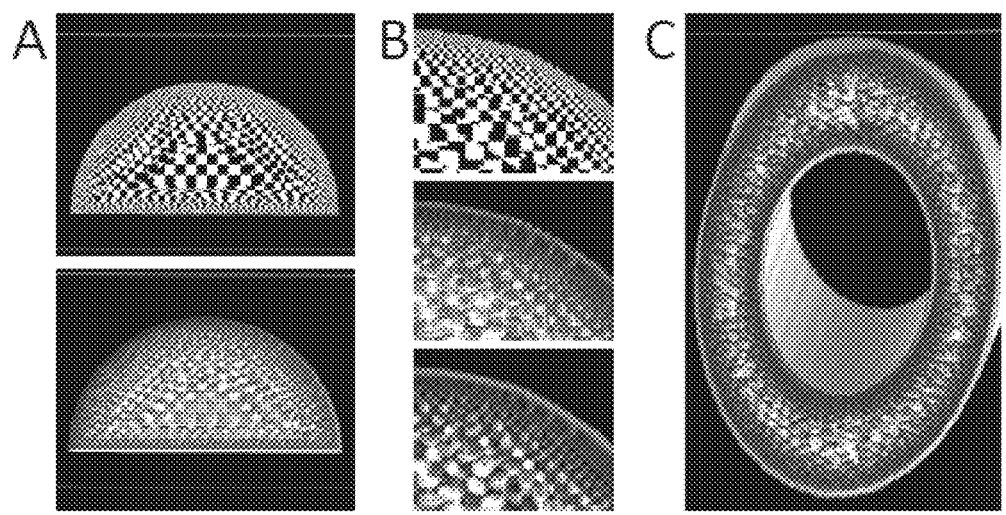
FIG. 12 provides photomicrographs of a patterning algorithm of varying checkerboards applied to a complex shape.
Figure 14:
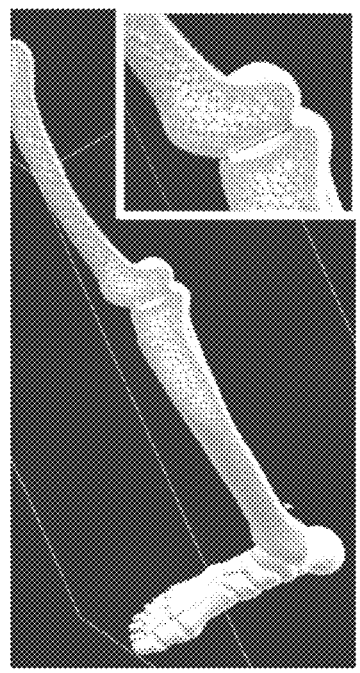
FIG. 14 shows possible subpatterning arrangements for a human lower limb model.

FIG. 10A shows a theoretical rendering of the internal structure of a simple cube as a result of varied subpatterns of light exposure. In this case, the light was modulated in a checkerboard fashion as a function of a voxel's distance from the cube's surface: larger checkerboards were used for more internal portions of the cube vs. smaller sizes for regions of the cube closer to the surface. The magnified images in the lower panels, below the overall view, in FIG. 10A also demonstrate how this subpatterning of light can interact with pre-polymer solutions of different properties in terms of material characteristics such as polymerization efficiencies, macromer concentrations, and molecular weights, among others. This could yield finer detailed structures or alternatively result in more diffuse internal patterning. As FIG. 10B illustrates, the same exposure pattern (top image) could theoretically result in different internal morphologies (shown in the center and lower images of FIG. 10B), depending on the material used. FIGS. 11 and 12 provide examples of the same patterning algorithm, e.g., varying checkerboards, applied to more complex shapes, e.g., a toroid. This subpatterning can be applied to complex macroscale structures to locally modulate porosity and diffusivity. One approach may be to increase pore sizes for more internal deeper regions to counteract low diffusion rates, thus "normalizing" diffusivity throughout the bulk structure. Similarly, localized differences in mechanical properties, such as elastic moduli, could be patterned to influence the fate and phenotype of cells encapsulated within these printed constructs. To provide another example, the subpatterning technique can be applied as illustrated in the biomimetic examples presented in FIGS. 13A-13C, showing a rat brain (FIG. 13A—CAD design) and possible subpatterning arrangements at different "layers" or "slices" (FIGS. 13B and 13C), and a human lower limb model (FIG. 14).

EXAMPLE 1

Brain-on-a-Chip

Figure 7:
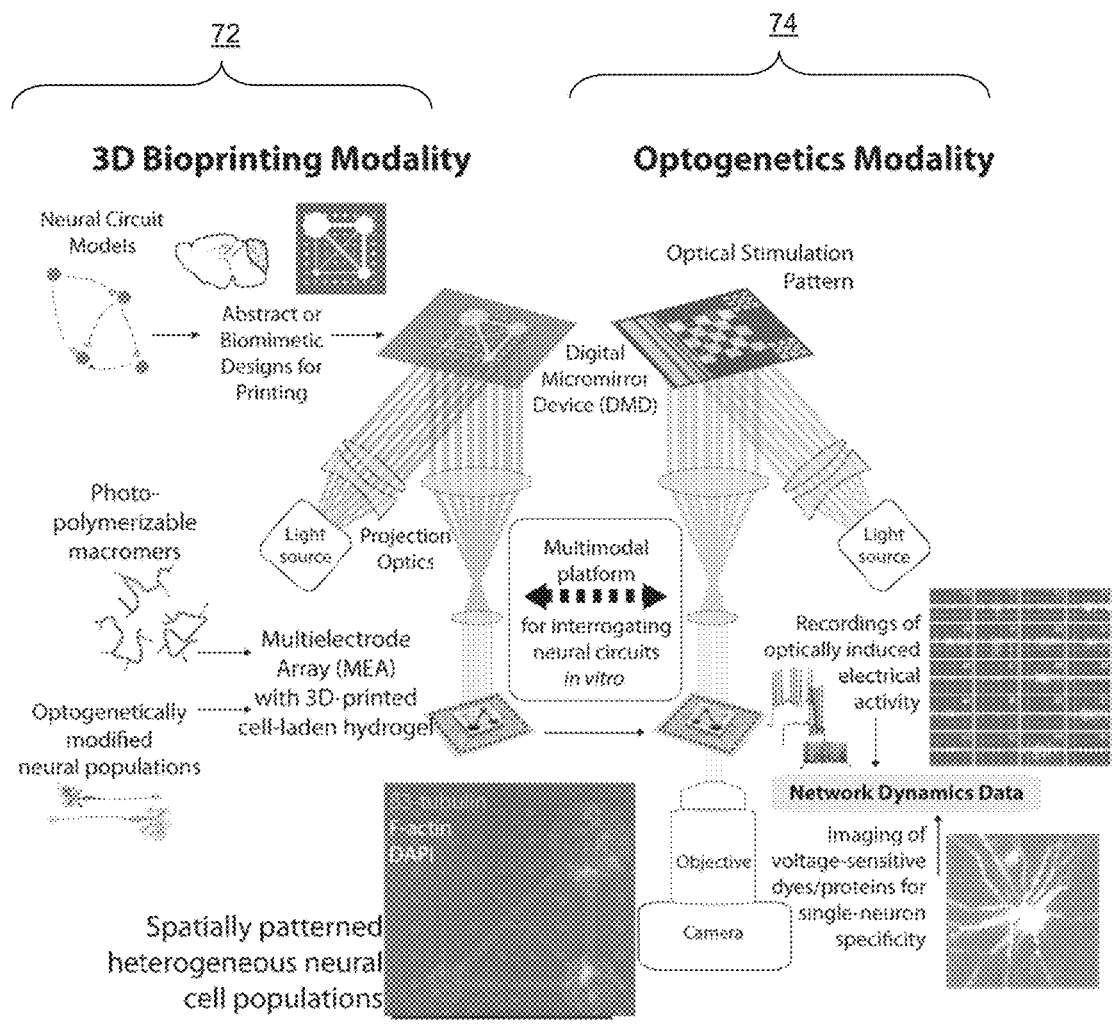
FIG. 7 is a diagram of a brain-on-a-chip platform that would integrate 3D heterogeneous neural cultures, optogenetics-enabled high-resolution stimulation, and parallel electrical and image-based recording of neural activity.

The L3PDOP platform described above yields two powerful modes of operation, which are diagrammatically illustrated in FIG. 7. The first modality 72 provides for 3D microscale bioprinting of biological substrates via dynamic stereolithography. The second modality 74 provides for optogenetic control of neurons with high spatiotemporal resolution. Stereolithographic 3D bioprinting (mode 72) using the printing platform described with reference to FIG. 1A and FIGS. 2A-2C provides for photopolymerization of multiple biocompatible materials (e.g., PEGDA, MeHA, GelMA) and facilitates cell encapsulation within these structures. Additionally, these materials—along with their incorporated cell types—can be used heterogeneously in the same scaffold to provide 3D patterned co-culture substrates, thus facilitating the study of neuronal/glial interactions.

Importantly, the inventive platform is capable of functioning not only in the fabrication and optogenetic stimulation modalities but also for recording network activity across multiple domains: 1) multi-electrode arrays (MEAs)—on which the 3D neuron network structures are printed—allow orthogonal recording of electrical activity concurrent with optogenetic stimulation; and 2) fluorescent imaging of voltage-sensitive dyes and proteins can be simultaneously performed using the same or similar light source utilized for bioprinting, thereby enhancing the single-neuron resolution of network activity.

In this example, the objective is the creation of a brain on a chip platform that integrates 3D heterogeneous neural cultures, optogenetics-enabled high-resolution stimulation, and parallel electrical and image-based recording of neural activity. In addition, the fabrication methods utilized in this platform offer control over both the topographical complexity and the cellular and material composition of the neural environment, thereby allowing for the potential for systematically-controlled increases in complexity.

The goal of studying isolated neural cultures is to examine and probe a simple in vitro system that can represent physiologically relevant models. Although a large sum of neurophysiological data that details the function of monolayers of neurons is widely available, the conditions used for these cultures vary drastically from the ones present in native tissue. Taking into consideration the vast literature indicating the effect of environment on neural function, it is reasonable to assume that the behavior of 2D cultures is not a good representation of the complex system that is the in vivo neural physiology. Recent work demonstrates that growing neurons in 3D scaffolds with incorporated glia provides drastic morphological and electrophysiological differences in comparison to neural networks grown in 2D cultures. This is attributed to the fact that 3D neural scaffolds better resemble the complex neural environment present in vivo.

EXAMPLE 2

Neural Clusters from iPSCs

The inventive L3PDOP platform finds myriad applications in fundamental neuroscience research, clinical diagnostics, screening of novel drug candidates, and comparative investigations of artificial versus biological neural networks in conjunction with neuromorphic hardware (e.g. "brain-on-a-chip" devices). The inventive printing technique enables facile, rapid fabrication of 3D hydrogels that support the culture of iPSC-derived neurons with the following capabilities: 1) 3D patterning of hydrogel microenvironments via dynamic optical stereolithography for high-throughput scaffold fabrication that is co-registered with MEAs at high precision; 2) directed arrangement of neural clusters and modulation of cell alignment, growth, and connectivity via hydrogel composition, geometry, and dimensions; 3) support for functional connectivity as demonstrated by positive expression of associated biomolecular markers, and 4) spontaneous electrical activity during long-term culture of neural populations that corresponds with their spatial arrangement on the 3D printed hydrogel-MEA substrates.

Stereolithographic 3D bioprinting as described herein allows for photopolymerization of multiple biocompatible materials. For example, but without limitation, such materials include gelatin methacrylate (GelMA), methacrylated hyaluronic acid (MeHA), poly(ethylene) glycol diacrylate (PEGDA)). The printing method also facilitates cell encapsulation within these structures. Other classes of specialized photo-crosslinkable polymers can include conductive polymers, such as PANI-PAAMPSA [polyaniline-poly(2-acrylamido-2-methylpropane sulfonic acid)]. (See, e.g., Yoo, J. E. et al., "Directly patternable, highly conducting polymers for broad applications in organic electronics", $PNAS$, (2010) 107(13), 5712-5717). Additionally, these materials—along with the incorporation of various cell populations—can be used heterogeneously in the same scaffold to provide multi-component 3D patterned co-culture substrates, thus facilitating the study of complex cell-cell and cell-ECM interactions.

Figure 15:
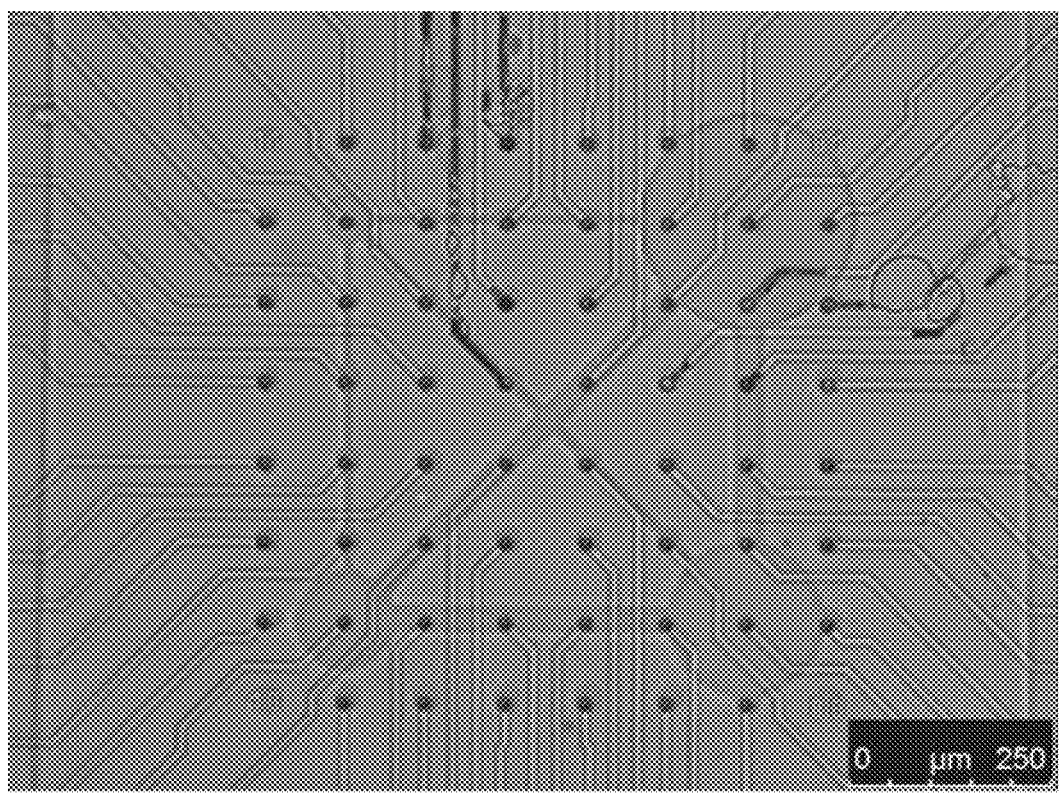
FIG. 15 is a micrograph showing GelMA scaffolds with culture wells, interconnecting paths/channels, and countersinks for the electrode sites aligned with an MEA.

For the 3D patterning of neural progenitor cells (NPCs), hydrogels were made using photopolymerizable macromer solutions of 5 to 7.5% gelatin methacrylate (GelMA) in DPBS. Via the aforementioned stereolithographic technique, connected microwell arrays of different radii (5 to 300 µm), depths (100 to 500 µm), and channel widths (5 to 50 µm), were printed. The GelMA hydrogel scaffolds were used for culture and patterning of iPSC-derived NPCs. UV-light mediated polymerization occurred within 30 to 60 seconds of patterned exposure to produce scaffolds 5 mm×3 mm×100 to 500 µm. Using a microscope camera mounted below the projection platform, transparent MEAs were aligned with the image projected from the DMD by translating the linear stages. 3D GelMA scaffolds with pre-defined culture wells, interconnecting paths/channels, and countersinks for the electrode sites were precisely aligned with the MEA to allow for directly registered printing of hydrogels, as shown in FIG. 15.

Figure 16:
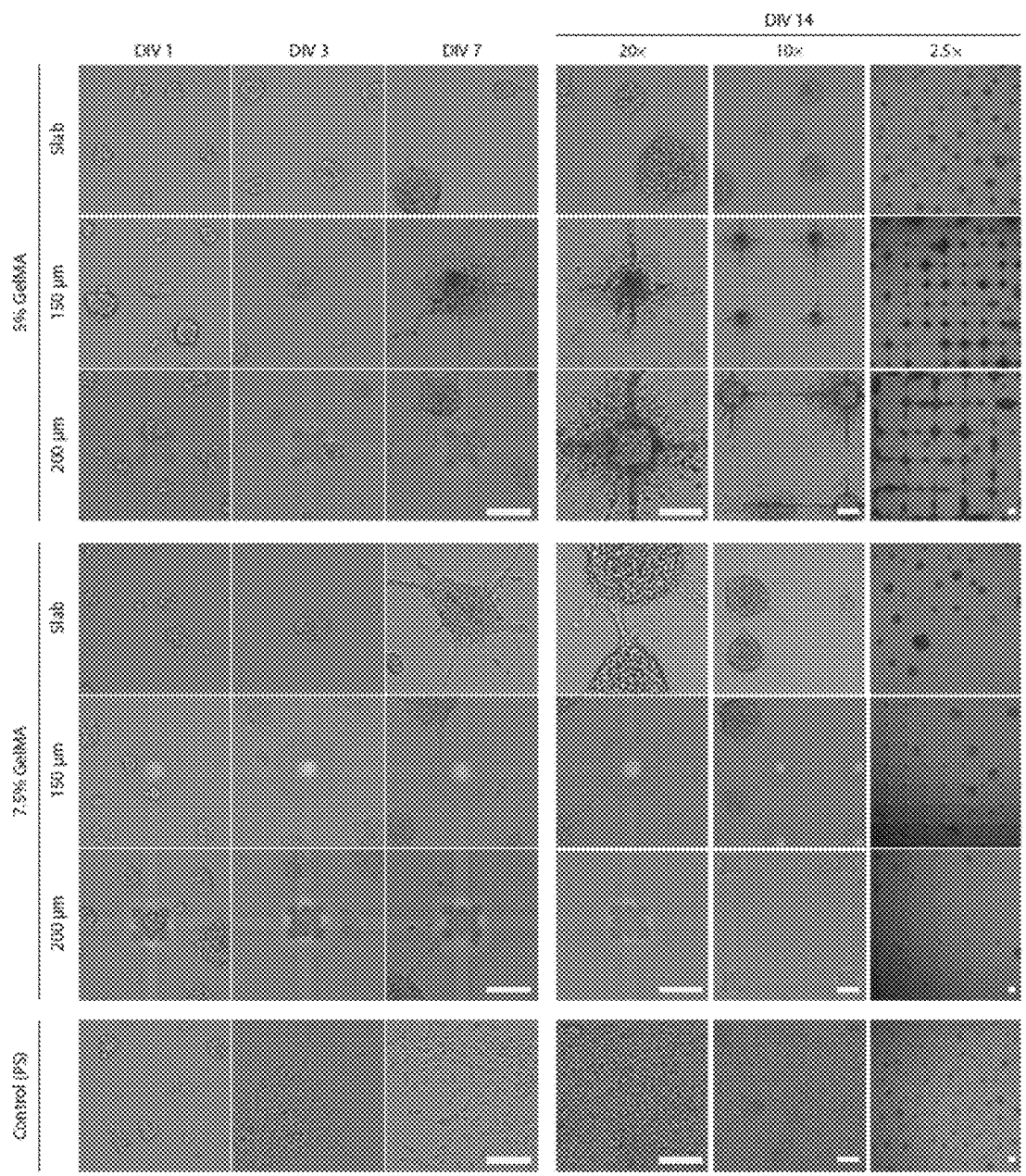
FIG. 16 is a set of micrographs showing NPCs aggregated within the wells and extended neurites following scaffold printing using different GelMA concentrations relative to a control.
Figure 17:
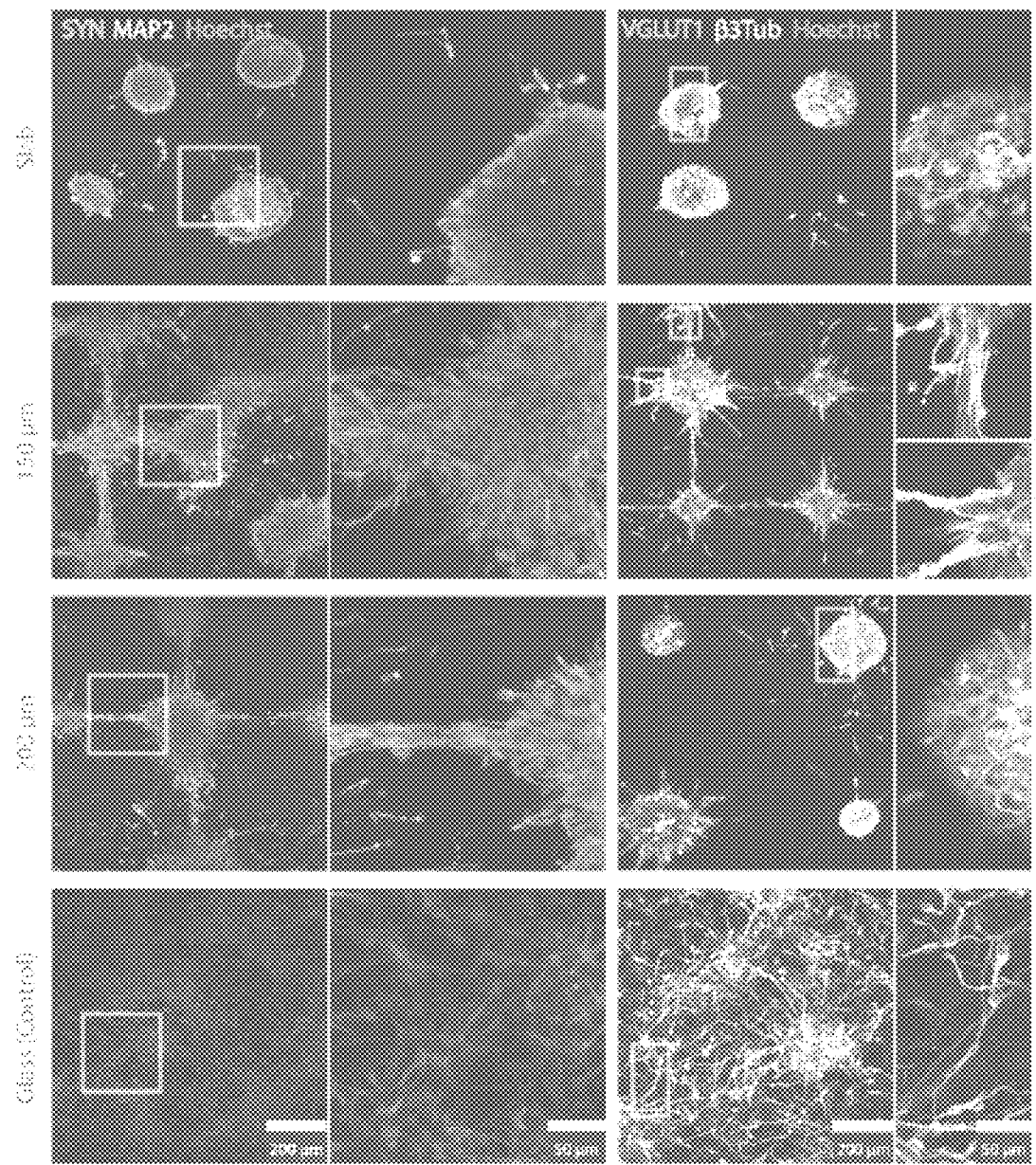
FIG. 17 is a set of micrographs of neural cell cultures in the inventive scaffolds labeled to assess cell morphology, function, and synaptic connectivity after one month, relative to glass control.

When seeded, NPCs aggregated within the wells and extended neurites along the guidance channels to varying degrees depending on the water content of the material. Percent concentration of GelMA (5% vs. 7%) had a substantial effect on cell spreading, proliferation, alignment, and connectivity (FIG. 16). After one month of culture, scaffolds were fixed in 4% paraformaldehyde, and immunofluorescently labeled using antibodies for synapsin, VGlut1, MAP2, GFAP, and beta-III tubulin to assess cell morphology, function, and synaptic connectivity. As shown in FIG. 17, markers of functional connectivity exhibited differences based on substrate type and patterning dimensions, with higher levels of synapsin expression observed in cultures on the GelMA substrate when compared to the glass control. Sparse expression of VGlut1 was also observed, suggesting early commitment of some neurons to a glutamatergic phenotype.

Figure 18:
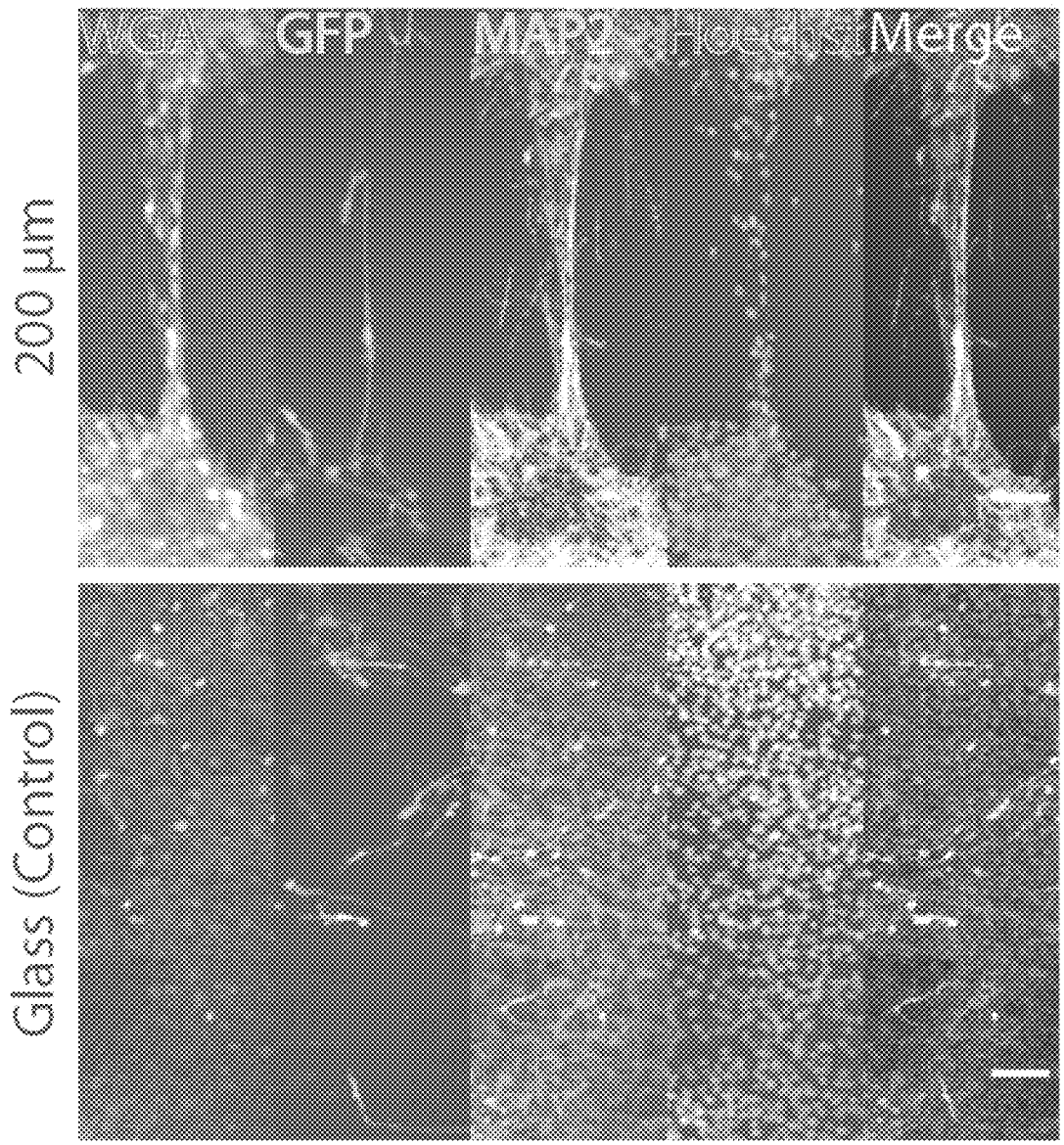
FIG. 18 is a set of micrographs of neurons cultured in the inventive scaffolds, labeled to assess functional connectivity relative to glass control.
Figure 19:
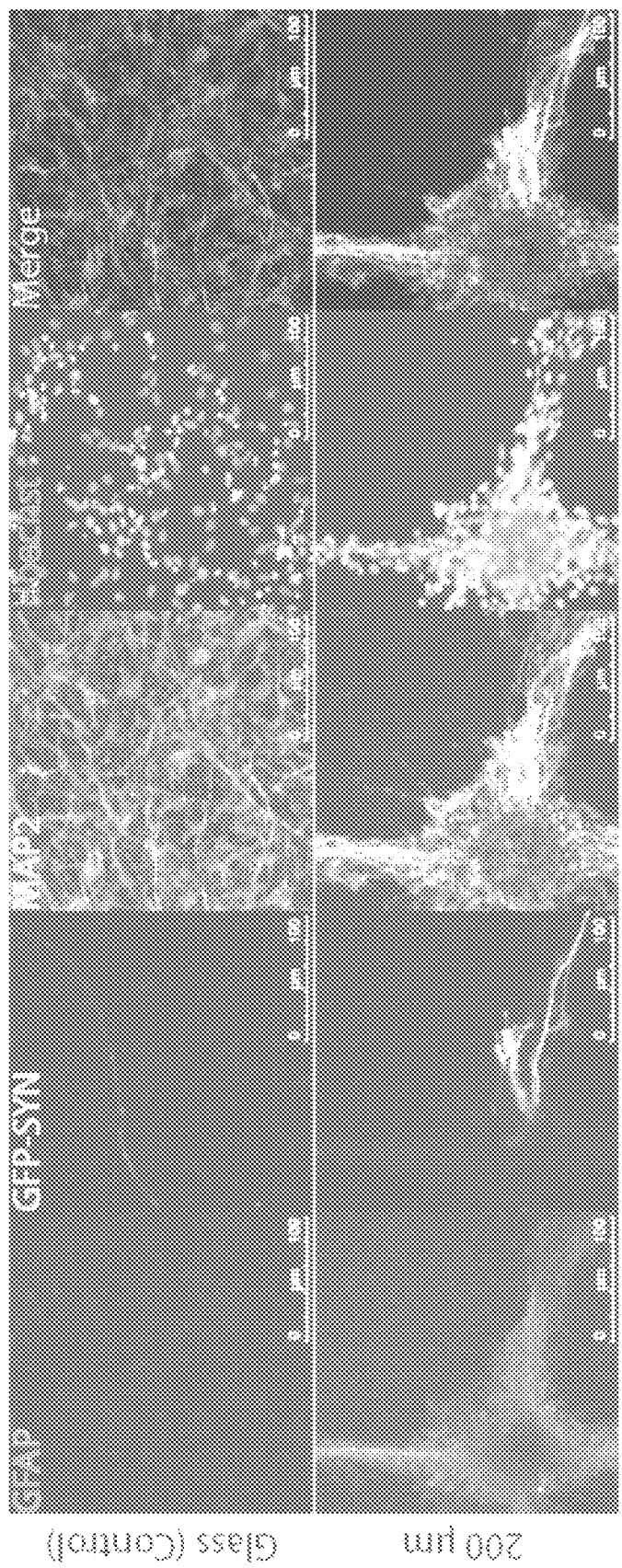
FIG. 19 is a set of micrographs of neurons cultured in the inventive scaffolds labeled to assess synapsin expression relative to a glass control.

To further assess functional connectivity, neurons were transfected with plasmid DNA for co-expression of wheat germ agglutinin (WGA) and green fluorescent protein (GFP) reporter (FIG. 18). Neurons staining positive for WGA but negative for GFP suggest that post-synaptic uptake of WGA has occurred through functional connections between WGA-expressing and non-expressing populations. Furthermore, synapsin expression was additionally assessed via a plasmid for co-expression of GFP that is localized with synapsin expression (FIG. 19). As discussed previously, greater expression is seen in the 3D scaffold conditions (lower panel) versus the glass control (upper panel).

Figure 20A:
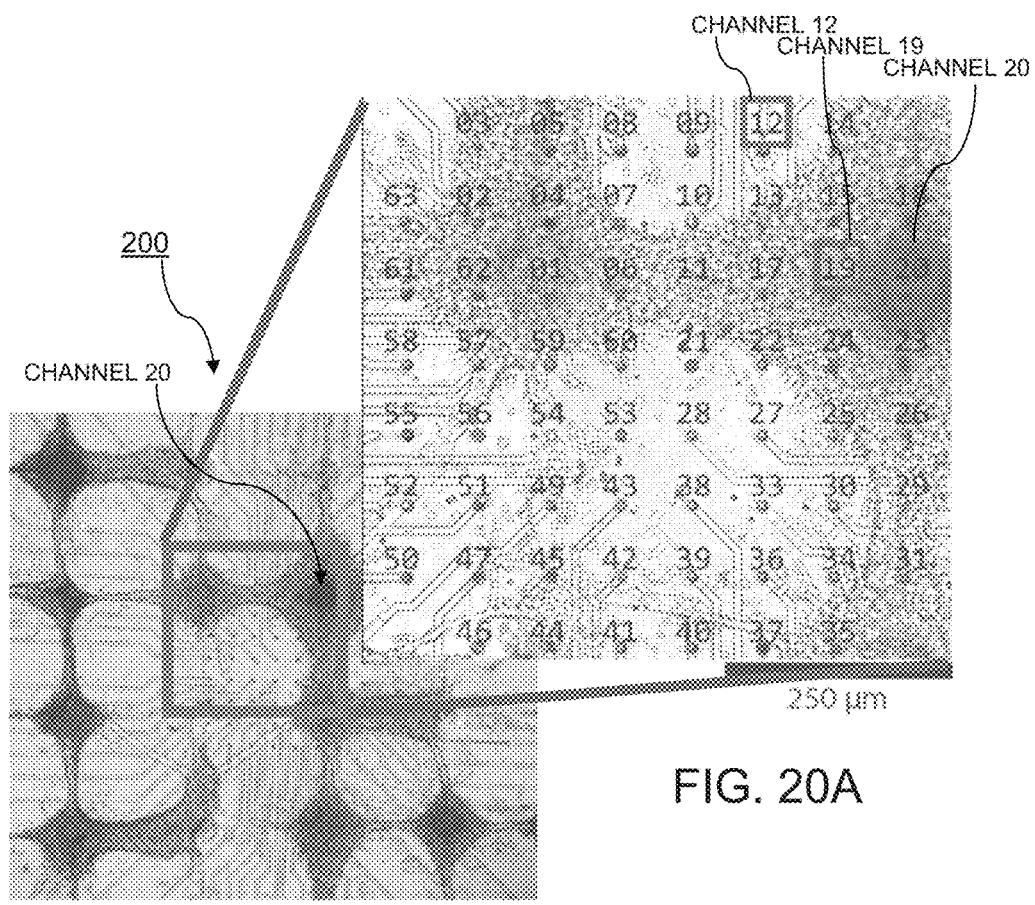
FIG. 20A is micrograph of a multi-electrode array (MEA) imprinted with neural clusters according to an embodiment of the invention, where the inset is a zoomed-in image of the center of the well cluster.
Figure 20B:
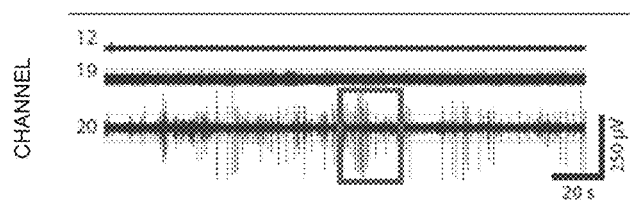
FIG. 20B is a plot of the measured spiking activity at channels 12, 19 and 20 within the MEA.
Figure 20C:
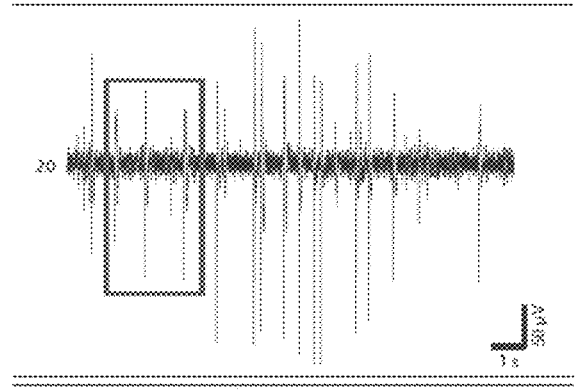
FIGS. 20C and 20D are plots of selected time sequences for channel 20.
Figure 20D:

The patterned neuronal networks also demonstrated spontaneous, spatially-dependent electrical activity. When mapped to the recording channels, the MEA electrode locations that corresponded with the center of the neural clusters within the hydrogel wells exhibited the highest activity. As shown in FIGS. 20A-20D, channel 20 ($3^{rd}$ row, $8^{th}$ column in the zoomed in segment of FIG. 20A) corresponds with the center of the large well cluster in the upper right corner of the MEA 200 (FIG. 20A) and shows high activity compared to other channels (e.g., highlighted channels 12 and 19) that are nearby but in sparsely populated areas (FIG. 20B). Subplots of the spiking activity shown at shorter time scales (FIGS. 20C-D) demonstrate wave profiles that are characteristic of local field potentials. This is consistent with the setup of a hydrogel placed on top of the MEA and reflects the integrated activity in the well region.

EXAMPLE 3

Integration with 3D-Printed Conductive Polymer Electrodes

Figure 21A:
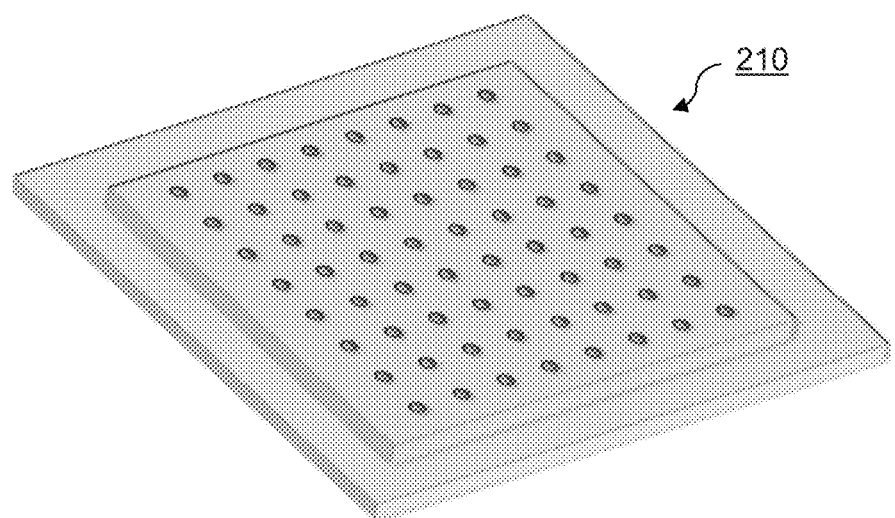
FIGS. 21A and 21B are diagrammatic views of an exemplary MEA arrangement with standard flat electrodes versus 3D printed conductive polymer electrodes of varying sizes, respectively.
Figure 21B:
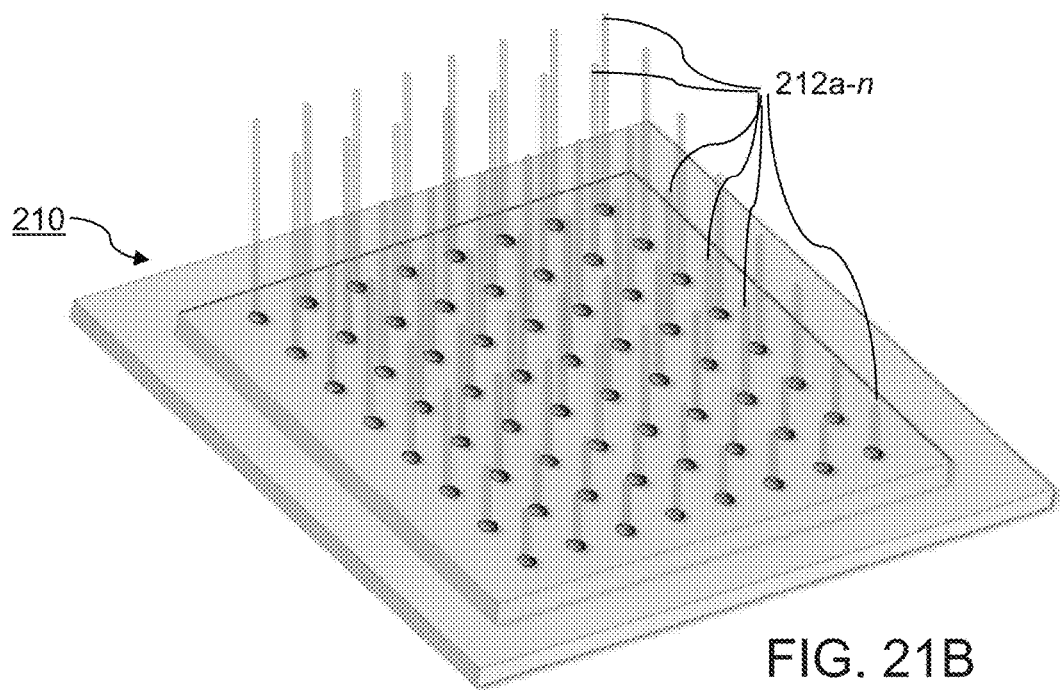

High-density 3D recording of the neural network can be achieved by using the stereolithographic technique presented herein to incorporate biocompatible conductive polymers, such as PANI-PAAMPSA, at precise spatial arrangements to transmit neural electrical signals to the multi-electrode array (MEA) substrate. FIGS. 21A and 21B illustrate one possible spatial arrangement and varying electrode lengths, respectively. FIG. 21A shows a simple grid-like array in MEA 210, with uniformly spaced rows and columns of flat electrodes of similar heights, while FIG. 21B illustrates electrodes 212A-n of different lengths (heights) extending from the same grid. As will be readily apparent to those in the art, different geometrical layouts and varying electrode heights can be constructed by selection of appropriate printing patterns, conditions, and materials. Compared to conventional flat electrodes on MEAs, which can directly access only the limited network dynamics data available on the periphery of the 3D neural network, 3D-printed conductive hydrogel electrodes can probe the network internally at various spatial locations throughout the neuron-laden scaffold. Furthermore, the conductive polymer electrodes can provide a conduit for electrical neurostimulation in a modality that is orthogonal to the optogenetically-mediated stimulation and thus can be independently and/or simultaneously applied. This can enable investigation of the effects of long-term potentiation (LTP) or long-term depression (LTD) within neuronal subpopulation in terms of the network's response to concurrent activation via the alternate stimulation modality.

EXAMPLE 4

Adaptive, Reprogrammable Biological Logic Gates, Perceptrons, and Hybrid Neural Networks Compared to conventional von Neuman architectures, a synthetic analogue to neural computation exhibits far greater performance in tasks such as visual identification and speech recognition. Within the cognitive and computational sciences, software algorithms (e.g., artificial neural networks) and hardware implementations of neural circuits (e.g., neuromorphic hardware) have been developed to engineer a computational substrate with equivalent capacity. These technologies have been widely applied towards solving computationally intensive problems, such as data mining, automated medical diagnosis, and self-learned game strategies, as well as to reveal the potential mechanisms that underlie the various dimensions of human cognition. However, the degree to which the specific computational processes and learning algorithms of these synthetic systems truly represent their biological counterparts is still largely unknown. The integrated neural fabrication platform described herein can provide techniques for bridging this gap and for developing novel hybrid artificial/biological neural network devices that may yield computational power not yet realized by either synthetic or natural versions of these networks in isolation.

Figure 22A:
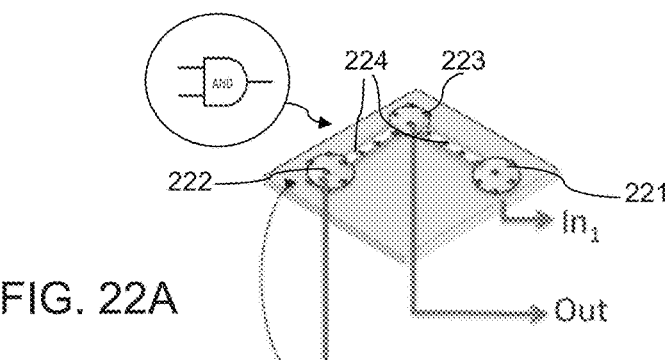
FIGS. 22A-22B illustrate an exemplary biological neural network creating using the inventive platform configured for implementing an AND logic gate.
Figure 22B:
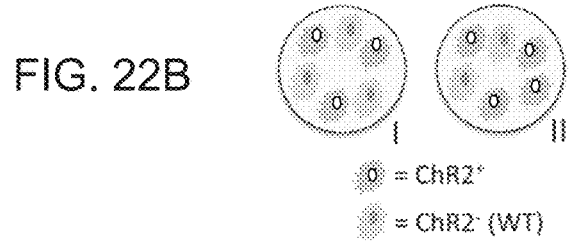
Figure 22C:
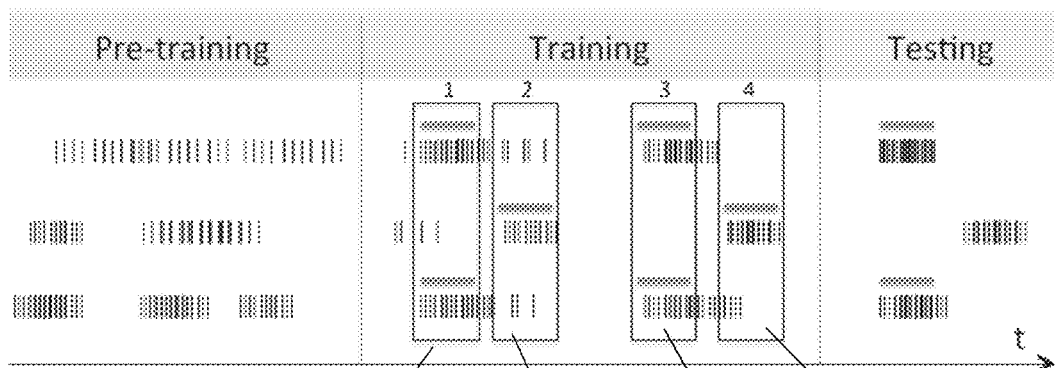
FIG. 22C illustrates an exemplary training and testing sequence with time.
Figures 22D, 22E:
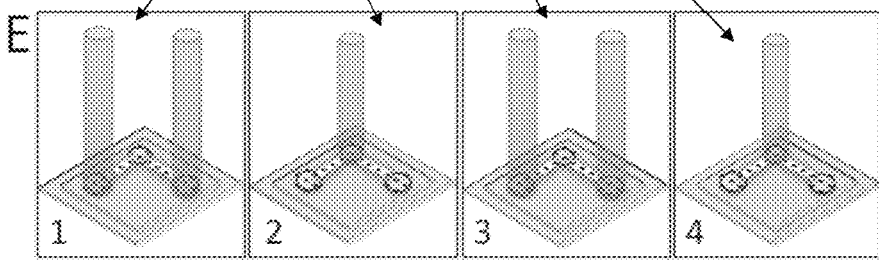
FIG. 22D shows a truth table for an AND logic gate.
FIG. 22E illustrates an exemplary training procedure.

One embodiment of a biological neural network created using the invention described herein is a logic gate consisting of two input nodes 221, 222, one output node 223, and two channels 224 (i.e., edges, per graph theory) between each of the input nodes and the output node, as shown in FIG. 22A. As shown in FIG. 22B, each node contains a neural population comprising a number of neurons (n≥1) of various types, including neurons that are optogenetically modified with light-responsive ion channels, e.g., channel-rhodopsin-2 (ChR2) (sensitive to blue light) or halorhodopsin (sensitive to green/yellow light) to enable light-mediated depolarization or hyperpolarization, respectively, as appropriate. (See, e.g., F. Zhang et al., "Optogenetic interrogation of neural circuits: technology for probing mammalian brain structures", Nat Protoc 5, 439-456 (2010).) In the example of FIG. 22B, ChR2$^+$ and wild type ChR2$^-$ are used. Each channel can guide neurite connections from one node to another. Once the neural culture has matured, the synaptic connectivity of this simple neural network can be employed to entrain a designated output in response to provided inputs, e.g., a classic AND logic gate. The corresponding truth table for the AND gate is provided in FIG. 22D. FIGS. 22C and 22E illustrate an exemplary training protocol, which can be specified in terms of stimulus modality (e.g., optical or electrical), stimulus duration, input-to-output stimulus latency, stimulus strength, number of trials, inter-trial interval, etc., with a set number of trials defining a training epoch. The three rows of variously spaced vertical bars in FIG. 22C represent the spike raster plots generated by the three nodes throughout an example training protocol, with the top and bottom rows representing the input nodes and the middle row representing the output node. The horizontal lines that span above some subsets of vertical bars represent the periods during which light stimulation was active for that particular node. Arrows drawn from FIG. 22C to 22E indicate the different training conditions. After several training epochs, the biological neural network may alter its connectivity via purported Hebbian learning principles (i.e., synaptic plasticity), such as spike-timing dependent plasticity.

Figure 23A:
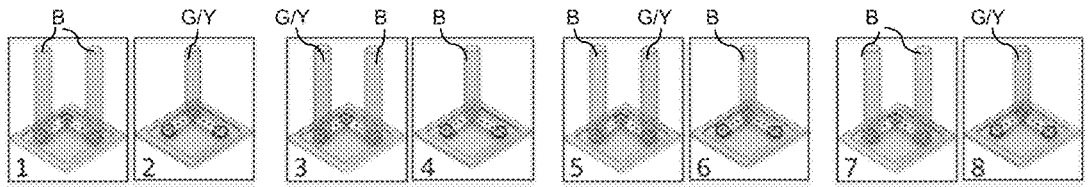
FIGS. 23A-23C illustrate an exemplary biological neural network creating using the inventive platform configured for implementing an XOR logic gate, where
Figure 23B:
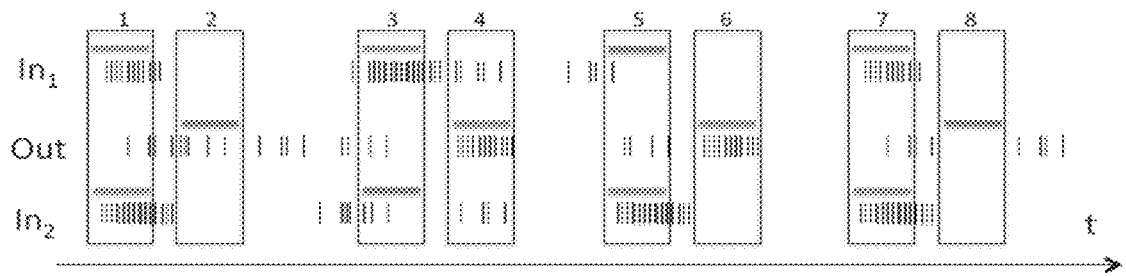
Figure 23C:
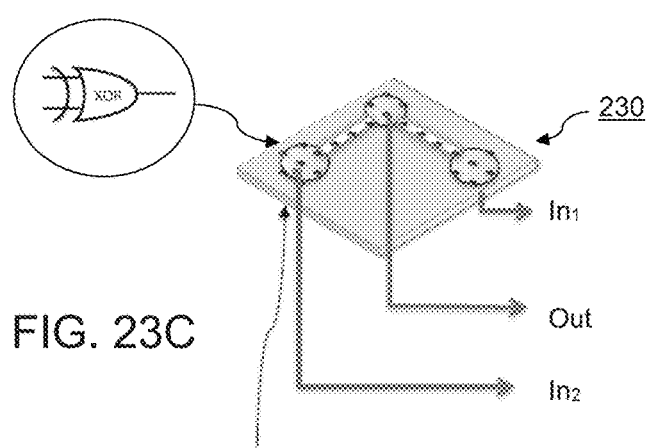
Figure 23D:
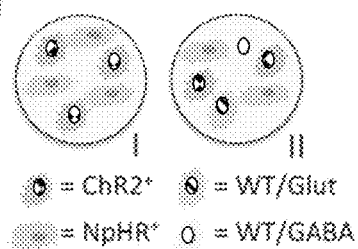
FIG. 23D shows a truth table for an XOR logic gate.
Figure 23E:
FIG. 23E is a set of theoretical ROC curves generated during testing of the neural network.

The logic gate may be subsequently retrained using a new truth table to convert the network into a different logic gate type, e.g., converting it from an AND gate to an exclusive-OR (XOR) gate, in which the output will be "1" if and only if one input is "1" (FIG. 23D). The XOR gate training sequence is illustrated in FIGS. 23A (showing the MEAs) and 23B (showing the corresponding spike raster plots and associated periods of light stimulation), using blue ("B") and green/yellow ("G/Y") light. In this example, as shown in FIG. 23C, the MEA 230 is printed to include neurons modified with channelrhodopsin (ChR2) and halorhodopsin (NpHR) to provide depolarization/excitation and hyperpolarization/inhibition, respectively, in response to different colors of light, along with populations of wildtype ("WT", i.e., not light activated) excitatory and inhibitory neurons, e.g., glutamatergic ("Glut") and GABAergic ("GABA") neurons, at varying ratios within each node. The time or number of epochs needed to achieve sufficient conversion can be related to the various characteristics of the network. At the end of a training epoch, an entrained logic gate can be tested to determine the robustness of its output in relation to the desired truth table (FIG. 23D), and its performance can be quantitatively described, e. g., using a receiver operating characteristic (ROC) curve (FIG. 23E). These performance metrics can be compared to the stimulus and/or physical node parameters to derive phenomenological rules that describe the influence of these parameters on the networks' behavior.

Figure 24A:
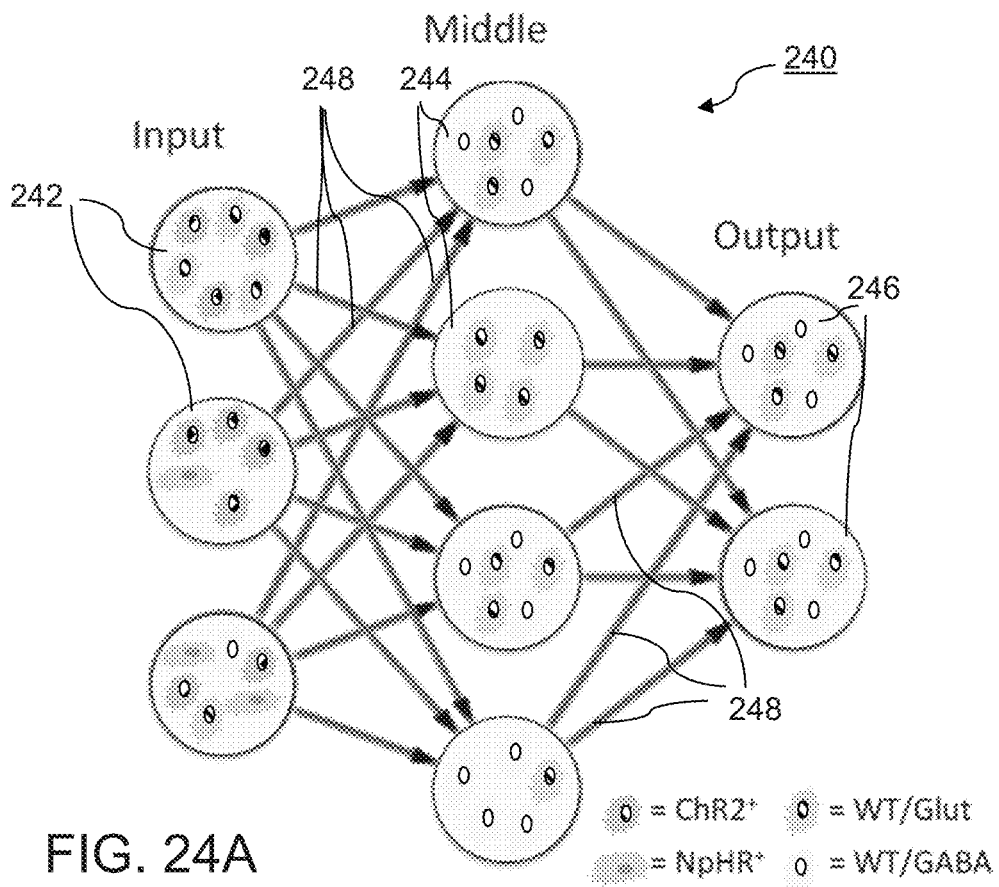
FIGS. 24A and 24B illustrate an exemplary neural network or perceptron structure and the corresponding MEA plate imprinted with neuron-laden hydrogels for implementing the neural network or perceptron structure according to an embodiment of the invention.
Figure 24B:
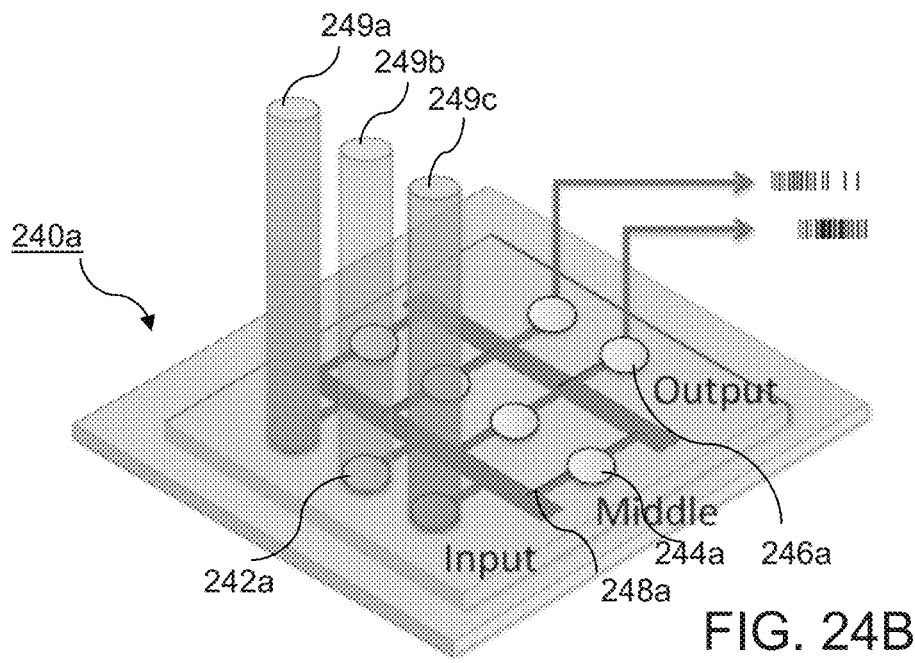

At larger scales, the biological neural network can be constructed to contain multiple numbers of inputs, outputs, and interconnections, along with multiple intermediary layers of nodes that ultimately link the input layer to the output layer. In this implementation, the biological neural network may resemble artificial neural network models, e.g., a perceptron. One example of a perceptron structure 240 is shown in abstracted form in FIG. 24A, with input 242, middle 244 and output layers 246 (connected by connectors 248) constructed using the same modified neurons used in the prior example: channelrhodopsin (ChR2$^+$) and halorhodopsin (NpHR$^+$), plus wild-type glutamatergic (Glut) and wild-type GABAergic (GABA) neurons. FIG. 24B diagrammatically illustrates the MEA plate 240a imprinted with neuron-laden hydrogels using the inventive 3D printing platform to implement biological perceptron 240, with corresponding input 242a, middle 244a and output 246a layers. The multi-branched grid 248a connecting the nodes of the three layers represents guidance channels printed within the hydrogel to facilitate interconnectivity as would be realized in a physical implementation of the abstracted illustration in FIG. 24A. This biological perceptron can be compared to its synthetic equivalent to determine the degree of correspondence between the in vitro and in silico implementations. Furthermore, the parameters of the nodes can be tuned by defining the geometry of the scaffold during fabrication. Nodes and connecting channels can be modulated in physical terms, including but not limited to diameter, eccentricity, internode distance, channel width, and channel radius of curvature. The nodes and connecting channels can also be modulated in biochemical terms, including but not limited to hydrogel composition, concentration, functionalization with bioactive moieties, localized delivery of bioactive molecules, and light-triggered release of bioactive molecules. The activating columns of light 249a-c, as differentiated by differences in hue and opacity within the schematic, represent the modulation possible in terms of the light stimulus, including but not limited to intensity, duration, wavelength, number of pulses, and pulse width. In more complex implementations, the network may contain, for example, redundant channels or nodes of different shapes. Comparison to computational simulations of neural networks that include the relative spatial arrangement of the constituent neurons as a defining parameter in their models may further elucidate how spatial 3D patterning of neurons can influence the circuit behavior.

Using the described platform, neurostimulation can be provided either optically by projecting light onto optogenetically-modified neurons or electrically via the MEA interface. In the case of optogenetic activation, the neurons can be modified to yield populations that express different light-sensitive opsins to elicit varied electrical responses, e.g., channelrhodopsin-2 (ChR2) for depolarization/excitation versus halorhodopsin (NpHR) for hyperpolarization/inhibition. By incorporating heterogeneous populations of wildtype excitatory and inhibitory neurons, e.g., glutamatergic and GABAergic neurons at varying ratios within each node, as well as any of the myriad interneuron species either found in native tissue or synthetically engineered to exhibit more exotic or not naturally-realized behaviors, more complex models of network dynamics featuring inter-neuronal modulation via excitation or inhibition can be realized. Furthermore, the neurons may undergo optogenetic modification either before or after incorporation into the 3D scaffold. In the latter case, the scaffold material may be functionalized via 3D patterning to allow for localized transfection of plasmids encoding different opsins per a defined spatial arrangement. Finally, these scaffold, network, and stimulus parameters can be modulated in conjunction with other environmental changes, such as light-activated uncaging of neurotransmitters and administration of other mechanical, chemical, and/or biological stimuli that may influence the network's training efficiency, robustness, and overall dynamics.

In another experimental paradigm, assessing the long-term fidelity of the entrained biological neural network can provide information regarding its capacity to serve as a long-term biological substrate for memory. After undergoing the training sessions as previously described, a multi-well MEA plate or multi-chambered MEA microscope slide consisting of several in vitro biological neural networks may be kept in culture for an extended period per standard cell culture protocols. After defined time points, e.g., 1 to 4 weeks, the fidelity of the networks' entrained response can be quantified to determine longevity or volatility of the entrained response, i.e. the persistence of the embedded memory. This non-von Neumann model of integrated memory and computation serves the basis for many theoretical frameworks of human cognition and has recently been implemented in the context of hybrid CMOS-memristor neuromorphic circuits.

Figure 25A:
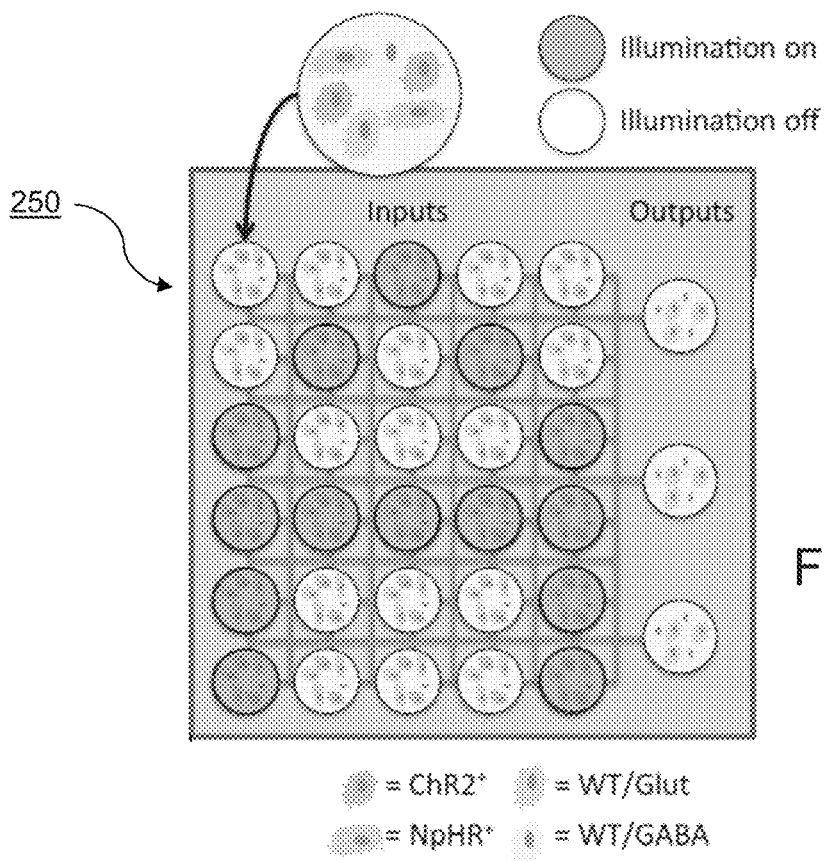
FIGS. 25A and 25B are diagrammatic views of a neural network computing system constructed according to an embodiment of the invention.
Figure 25B:
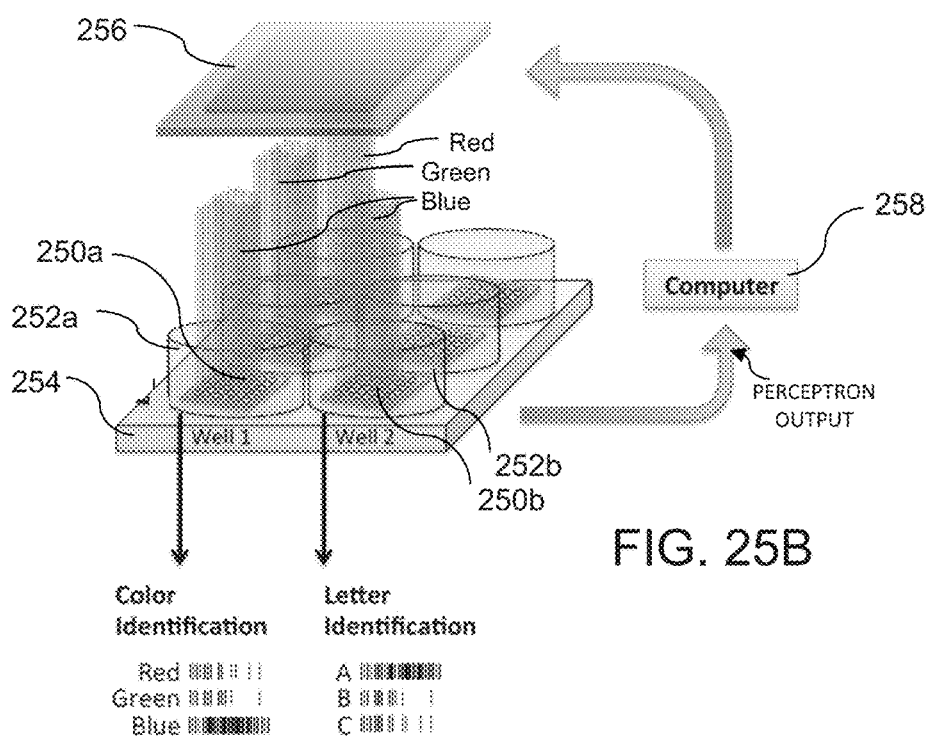

By integrating this high-throughput multi-well biological neural network within a larger hybrid artificial/biological neural network system, hierarchical and distributed computational algorithms can be implemented to utilize features of both types of neural architectures or to efficiently segment a larger complex job into perceptron-specific unit tasks. In one embodiment, each well 252a of a multi-well plate 254 (seen in FIG. 25B) can be entrained with a unique perceptron 250 to perform a specified subtask in response to different stimuli, e.g., illumination. Referring to FIG. 25A, which illustrates a single exemplary perceptron 250, in an identification task where the color and character of a letter must be computed for example, a blue "A", one well 252a in FIG. 25B may contain a perceptron 250a entrained to recognize the color of the stimulus while another well 252b includes a perceptron 250b that identifies the letter. Alternatively, multiple wells can be entrained with the same perceptron 250 to provide parallel replicate computation of a given stimulus to improve the collective accuracy of the system's output. Multi-well optical stimulation may be achieved through concurrent projection of multiple DMDs 256 or by using a mirror galvanometer to rapidly scan across multiple wells. Generally, this approach is akin to the modern implementation of multi-core CPUs to achieve parallel processing. Furthermore, an integrated computer processor 258 and accompanying algorithm may be used to implement more sophisticated computational capabilities, including but not limited to 1) a closed-loop feedback system where output provided by biological perceptrons can trigger changes in the illumination pattern projected by the DMD 256, or 2) output from the biological perceptrons providing input into an artificial perceptron or neural network implemented within the computer to create a hybrid biological-artificial neural network.

In another embodiment, due to the high-speed capacity of the projection device, the biological neural networks can be entrained to respond to more dynamic stimuli, for example, to self-learn video game strategies much in the way that artificial neural networks have been designed to self-learn these types of tasks, for example, using Google® Deep-Mind™. (See, e.g., V. Mnih et al., "Human-level control through deep reinforcement learning", *Nature* 518, 529-533 (2015).) In one implementation, a densely-patterned neural network of optogenetically modified neurons can be entrained by projecting the video feed from a game, such as the classic video game PONG®. The projected frames of the video game can entrain the network to "predict" the trajectory of a ball and thus provide output to direct the movement of the paddle at the end of the board. By entraining the network over several epochs of successful returns of the ball, the biological neural network may self-learn the optimal placement of the paddle to score a point. This entraining process may be enhanced by the concurrent administration of biochemical, e.g., dopamine, or other stimuli that strengthen the synaptic connections formed during a successful network response. The application of these large-scale self-learning biological neural networks may serve to recapitulate the intertwined memory and computational mechanisms of the human visual system.

EXAMPLE 5

In Vitro Models of Canonical Neural Circuitry in Systems Neuroscience Research The in vitro culture and interrogation of isolated neuronal populations forms a core platform broadly utilized throughout neuroscience research. The ability to forward engineer (i.e., deterministically construct patterned neuronal connections) is essential for corroborating evidence of connectome models derived via reverse engineering of existing native neural circuitry (i.e., in vivo recordings and brain imaging at various scales). True recapitulation of the anatomical features contributing to hypothesized canonical circuits relies on the ability to systematically pattern heterogeneous neuronal populations in their appropriate relative spatial arrangements. The unique methods described herein for constructing these 3D neural network structures have the potential to offer systematically controlled increases in complexity that is difficult to realize using conventional isolated neural populations. Furthermore, the incorporation of high-density 3D recording via the integrated printing of conductive polymer electrodes enables measurement of network dynamics in the proper spatial context, while using soft biocompatible hydrogels that feature mechanical properties that are closer to those of tissue in vivo. Using a heterogeneous population of neural cell types that reflect the composition found in native neural circuitry, the 3D patterning approach presented herein can be applied towards creating compartmentalized and/or systematically reduced representations of canonical in vivo neural systems. These in vitro constructs could then be used to assess the functional significance of various system components in a more accessible form to determine, for example, the individual and collective contributions of neural subpopulations in higher-level cognition and behavior.

EXAMPLE 6

Diagnostic and Drug-screening Platform

A major obstacle in studying neurological disorders such as Alzheimer's or Parkinson's diseases lies in accurately modeling their pathophysiology in a benchtop lab setting. Although animal models provide valuable insight into disease processes in vivo, ethical and technical limitations often prevent full translation of experimental findings into the clinical context. Recent advances in tissue engineering—particularly in 3D bioprinting and induced pluripotent stem cells (iPSCs)—provide new approaches for investigating neuropathologies in vitro. iPSC technology enables researchers to generate stem cells using adult cells unique to any individual. These iPSCs can be differentiated into neurons that reflect a disease phenotype specific to the patient from whom the iPSCs are derived.

3D culture environments resembling the native milieu in terms of biomaterial composition and mechanochemical properties can lead to neural cultures that correspond more closely with native systems and thus provide improved clinical relevance. Emerging evidence suggests that when compared to 2D substrates generated using conventional cell-culture arrangements such as Petri dishes, 3D microenvironments consisting of biocompatible hydrogels aid cells in more accurately portraying a diseased neural state (See, for example, S. H. Choi et al., "A three-dimensional human neural cell culture model of Alzheimer's disease," *Nature* 515, 274-278 (2014)). However, challenges remain in systematically patterning and probing 3D neural cultures to elucidate relationships between collective cell physiology and emergent electrical behavior. Multi-electrode arrays (MEAs) and voltage-sensitive fluorescent imaging, as well as optogenetic tools for stimulating neurons via light, are well-established techniques for recording neural activity in response to stimulation, but their application to in vitro 3D systems has been limited.

In one embodiment of the invention, the integrated platform for 3D bioprinting, optoelectric stimulation/recording, and fluorescence imaging is applied towards the construction and interrogation of in vitro neural disease models. The projection printing technology facilitates both the rapid 3D printing of neuron-laden hydrogels directly onto multi-well MEAs, including the MED™ Probe available from Alpha MED Scientific, Inc. (Berkeley, Calif., US) and the M768-KAP™ series available from Axion BioSystems (Atlanta, Ga., US), and the subsequent optical stimulation of these constructs at high spatiotemporal resolutions with precise registration between the stimulation pattern and the previously printed 3D geometries. Use of the inventive optical 3D printing techniques, enables the incorporation of complex topographies, composite biomaterials/nanomaterials, and heterogeneous cell populations with higher throughput when compared to inkjet-based 3D bioprinting, and with the inherent capability for optogenetic stimulation that is multiplexed with concurrent electrical recording and voltage-sensitive imaging. The ability to control the 3D arrangement, functional connectivity, and dynamic activation provides systematic assess to in vitro representations of neural circuits across both normal and diseased states. These approaches can help to elucidate causal relationships between pathological phenotypes and the anomalous network dynamics involved in neurological impairment.

Figure 26A:
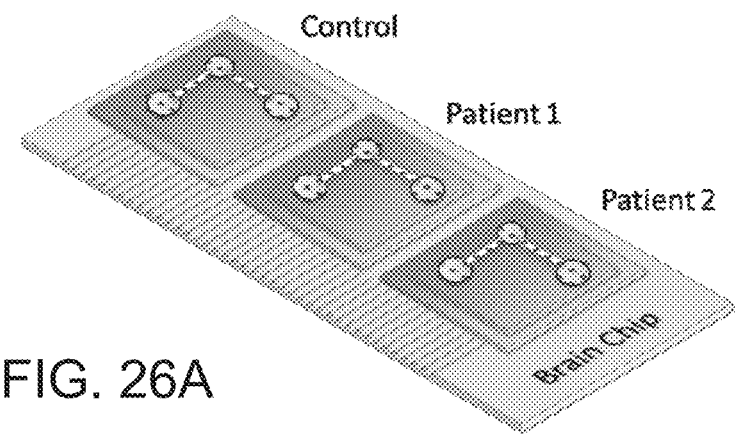
FIGS. 26A and 26B diagrammatically illustrate examples of custom MEA patterning capability enabled by the inventive 3D printing platform for use in high-throughput screening of parallel samples.
Figure 26B:
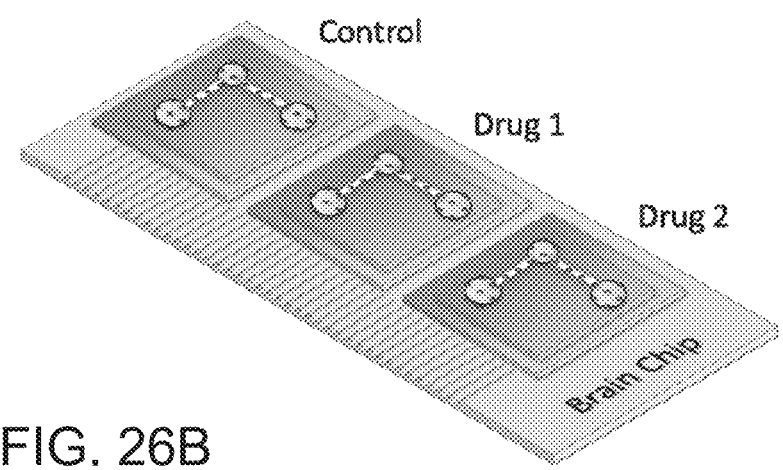

In a simple embodiment of this approach, a connectivity model featuring two nodes connected by a single channel may be constructed, wherein a node of a certain diameter contains a neural cluster of a correspondingly proportional number of neurons and the distance between the two nodes is modulated to influence the degree of connectivity between the two nodes. The level of connectivity between the two nodes can be quantified in terms of morphological arrangements (e.g., number of synapses per neuron) and functional activity (e.g., cross-correlated spiking/burst activity). Other embodiments may include multiple nodes, additional channels per node, and variations in node-channel geometry and topological arrangement. Comparisons between normal and diseased neural populations in terms of these quantitative measures may provide a diagnostic benchmark for assessing disease prognosis. Standardized metrics for connectivity can be assessed in a high-throughput fashion in multi-well MEAs that feature replicates of the same normal versus diseased neural constructs. These multi-well systems with incorporated highly-parallelized 3D printed neural circuits can be used for screening of drug candidates in the development of pharmaceutical treatments for neurological disorders. FIGS. 26A and 26B illustrate examples of custom MEA patterning capability enabled by the inventive 3D printing platform for use in high-throughput screening of parallel samples. Moreover, assessment of efficacy and safety of potential medications can be performed with patient-level specificity through the use of patient-specific iPSC-derived neural populations.

EXAMPLE 6

Cloud-based 3D Bioprinting and Neurostimulation Platform

Three-dimensional cell culture within biomaterial scaffolds has evolved to incorporate numerous aspects of the native tissue microenvironment, such as topographic patterning, heterogeneous co-culture populations, and dynamic modulation of scaffold properties. Yet, despite the novel avenues of investigation they provide, newer 3D approaches have seen limited use by the broader life sciences. Barriers include the knowledge base and capital investment required for implementing complex custom equipment. Research collaborations help overcome these hurdles via sharing of resources, but such efforts are often met with challenges in communication and efficiency as well as physical bottlenecks in long-distance sample and reagent transfer. Teams can often struggle to remain abreast of experimental details for project components outsourced to a collaborating lab. In the context of 3D bioprinting, a disconnect between one lab's design requirements and another lab's technical capabilities can lead to inefficient cycles of revision and rework, with an increased likelihood for experimental error, loss of data integrity, and misinterpretation of results.

To address these challenges, a web application framework can be used to extend the collaborative capacity of the integrated bioprinting, optical projection, and neurostimulation platform presented herein (or of other 3D printing platforms in general). This framework uses a "cloud-based" solution for current and future collaborators by providing:

1) a web application that enables shared creation, specification, and revision of custom 3D designs, associated printing parameters, and/or neurostimulation patterns that are stored on the cloud to enhance repeatability and reproducibility for both internal and external collaborating users;
2) extensions to the system's web application to include experiment workflows, such that all data regarding a sample's fabrication process and/or subsequent stimulation and/or recording as well as any other upstream preparation (e.g., reagent synthesis, genetic modification of cells, fabrication of the bare MEA substrate) and/or downstream experimental use (e.g., extended cell culture, drug administration, biochemical assays, confocal imaging) can be accessed securely, remotely, and simultaneously through cloud-based services;
3) multi-user real-time remote monitoring and control of the system to provide an in situ view of the sample and to enable real-time evaluation and feedback regarding the fabrication and/or stimulation of the scaffold to minimize design revisions and experimental error; and
4) cloud-based access to the computational capabilities of a patterned biological and/or hybrid (biological/artificial) neural network, as described previously in Example 4, via remotely controlled input (either via optical or electrical stimulation) and remote readout of the neural network's output (via MEA and/or imaging) either as part of a learning sequence to entrain the neural network or as part of a distributed computing model where the previously entrained and optimized network can be used for on-demand computation.

The foregoing disclosure provides novel approaches in both complex 3D biofabrication and dynamic molecular biosensing towards the investigation of poorly understood cell-cell interactions among heterogeneous cell populations. The 3D bioprinting platform of the present invention offers a transformational machine for creating biomimetic, functional tissues. The biosensors and single cell imaging should provide powerful tools to study molecular coordination in space and time in live cells. The integration of biosensing techniques of high sensitivity/specificity with 3D biomimetic tissue scaffolds will enable high-resolution monitoring of the dynamics of proteins, enzymes, subcellular organelles, and electrical activity in precisely engineered physical/chemical microenvironment. The technical impact of the micro-tissue-on-a-chip model lies in its immediate applications for early drug screening and personalized medicine. Measurement of neurotoxicity in neural populations, or analogously, cardiotoxicity in electrically active cardiac cell types, in response to drugs can address stringent drug testing requirements much earlier in the drug discovery process than currently possible. Such transformational micro-tissue model would markedly reduce the high cost of drug development, now a major economical roadblock to sustained progress in healthcare.

The invention claimed is:
1. A system for 3D microfabrication of a structure, comprising:
    a light source configured for projecting light within an optical path, the light source emitting light at a wavelength configured for initiating photopolymerization;
    a stage configured to support one or more containers containing a photopolymerizable material, wherein the stage is configured for movement along at least one axis;
    an optical assembly disposed within the optical path between the light source and the stage for projecting light toward an optical plane, the optical assembly comprising:
    a spatial light modulator configured for modulating the light responsive to a set of digital masks corresponding to layers of the structure;
    an optical tube having a window sealed at an end thereof, the window configured for immersion in the photopolymerizable material in the one or more containers to define a printing interface between the window and the photopolymerizable material, wherein the printing interface is substantially coincident with the optical plane;
    and
    a computer controller configured for generating control signals for:
    controlling the spatial light modulator to project a sequence of images corresponding to the set of digital masks toward the optical plane; and
    coordinating movement of the stage to move a position of the optical plane within the photopolymerizable material to sequentially project each image of the sequence to continuously generate the structure within the one or more containers by progressively photopolymerizing the photopolymerizable material along the at least one axis so that successive layers are polymerized on top of previously polymerized layers.

2. The system of claim 1, wherein the spatial light modulator comprises a digital micromirror device.

3. The system of claim 1, wherein the photopolymerizable material is a pre-polymer solution, and wherein at least a portion of the one or more containers contain different pre-polymer solutions.

4. The system of claim 1, wherein the computer controller further executes steps for coordinating movement of the stage to control a volume of pre-polymer solution between the window and previously polymerized layers.

5. The system of claim 1, wherein the one or more containers comprise wells within a multi-well plate.

6. The system of claim 1, further comprising an electrode or a multi-electrode array disposed within the one or more containers.

7. The system of claim 1, wherein the photopolymerizable material comprises a conductive polymer and at least a portion of the sequence of images corresponds to interconnecting structures aligned with one or more electrodes disposed within the one or more containers.

8. The system of claim 1, further comprising a second light source disposed within the optical path, the second light source emitting light at a wavelength configured to stimulate a photo-active biological material.

9. The system of claim 1, wherein at least a portion of the digital masks cause the spatial light modulator to generate subpatterns within selected layers of the structure.

10. A method for 3D microfabrication of a structure, comprising:
controlling the system of claim 1 using the computer controller to position the stage to immerse the window into the photopolymerizable material within the one or more containers and to project an image of the sequence of images toward the optical plane; and
simultaneously and continuously controlling, via a computer controller, the sequence of images and the stage movement to generate the structure by progressively photopolymerizing the photopolymerizable material along the at least one axis.

11. The method of claim 10, wherein the one or more containers comprise wells within a multi-well plate.

12. The method of claim 10, wherein at least of portion of the one or more containers contain different pre-polymer solutions.

13. The method of claim 10, wherein the one or more containers have an electrode or a multi-electrode array disposed therein.

14. The method of claim 13, wherein the photopolymerizable material comprises a conductive polymer and at least a portion of the sequence of patterns corresponds to interconnecting structures aligned with one or more electrodes.

15. The system of claim 1, wherein the window is treated to inhibit adhesion of the photopolymerizable material.

16. The system of claim 1, wherein the window is formed from a material selected from the group consisting of silica, sapphire, polydimethysiloxane (PDMS), transparent ceramic, and transparent plastic.

17. The system of claim 1, wherein the photopolymerizable material comprises a photo-crosslinkable hydrogel selected from the group consisting of gelatin methacrylate [GelMA], methacrylated hyaluronic acid [MeHA] and polyethylene glycol diacrylate [PEGDA].

18. A system for microfabrication of a structure, comprising:
a spatial light modulator disposed within an optical path of a light source and configured for modulating light from the light source responsive to a set of digital masks corresponding to layers of the structure;
projection optics disposed within the optical path and configured to focus the modulated light to an optical plane;
a stage configured to support one or more containers containing a photopolymerizable material within the optical plane, wherein the stage is configured for movement along at least one axis;
an optical tube disposed within the optical path and having a window sealed at the end thereof, the window configured for immersion in the photopolymerizable material to define a printing interface between the window and the photopolymerizable material, wherein the printing interface is substantially coincident with the optical plane; and
a computer controller having software therein for generating control signals for:
controlling the spatial light modulator to project a sequence of images corresponding to the set of digital masks onto the optical plane; and
coordinating movement of the stage to move a position of the optical plane within the photopolymerizable material to sequentially project each image of the sequence to generate the structure within the one or more containers by progressively photopolymerizing the photopolymerizable material along the at least one axis so that successive layers are continuously polymerized on top of previously polymerized layers.

19. The system of claim 18, wherein the spatial light modulator comprises a digital micromirror device.

20. The system of claim 18, wherein the photopolymerizable material is a pre-polymer solution, and wherein at least a portion of the one or more containers contain different pre-polymer solutions.

21. The system of claim 18, wherein computer controller is further operable for coordinating movement of the stage to determine a volume of pre-polymer solution between the window and previously polymerized layers.

22. The system of claim 18, wherein the one or more containers comprise wells within a multi-well plate.

23. The system of claim 18, wherein the one or more containers comprise wells within a multi-well plate.

24. The system of claim 18, wherein the photopolymerizable material comprises a conductive polymer and at least a portion of the sequence of images corresponds to interconnecting structures aligned with one or more electrodes.

25. The system of claim 18, wherein the photopolymerizable material comprises a photo-crosslinkable hydrogel selected from the group consisting of gelatin methacrylate [GelMA], methacrylated hyaluronic acid [MeHA] and polyethylene glycol diacrylate [PEGDA].

26. The system of claim 18, further comprising a second light source disposed within the optical path, the second light source emitting light at a wavelength configured to stimulate a photo-active biological material.

27. The system of claim 18, wherein at least a portion of the digital masks cause the spatial light modulator to generate subpatterns within selected layers of the structure.

28. The system of claim 18, wherein the window is treated to inhibit adhesion of the photopolymerizable material.

29. The system of claim 18, wherein the window is formed from a material selected from the group consisting of silica, sapphire, polydimethysiloxane (PDMS), transparent ceramic, and transparent plastic.

\* \* \* \* \*